US011666527B2

(12) United States Patent
Roberge et al.

(10) Patent No.: US 11,666,527 B2
(45) Date of Patent: *Jun. 6, 2023

(54) BIODEGRADABLE BLOCK COPOLYMER DRUG DELIVERY COMPOSITION

(71) Applicants: MEDINCELL, Jacou (FR); Christophe Roberge, Jacou (FR); Anthony Rech, Jacou (FR); Jean-Manuel Cros, Jacou (FR)

(72) Inventors: Christophe Roberge, Jacou (FR); Anthony Rech, Jacou (FR); Jean-Manuel Cros, Jacou (FR); Myriam Abbassi, Jacou (FR); Adolfo López-Noriega, Jacou (FR); Lea Pebrel, Jacou (FR); Audrey Petit, Jacou (FR); Juliette Serindoux, Jacou (FR)

(73) Assignees: MEDINCELL, Jacou (FR); Christophe Roberge, Jacou (FR); Anthony Rech, Jacou (FR); Jean-Manuel Cros, Jacou (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/631,586

(22) PCT Filed: Jul. 17, 2018

(86) PCT No.: PCT/EP2018/069442
§ 371 (c)(1),
(2) Date: Jan. 16, 2020

(87) PCT Pub. No.: WO2019/016236
PCT Pub. Date: Jan. 24, 2019

(65) Prior Publication Data
US 2020/0179518 A1 Jun. 11, 2020

Related U.S. Application Data

(60) Provisional application No. 62/533,370, filed on Jul. 17, 2017.

(51) Int. Cl.
| *A61K 9/00* | (2006.01) |
| *A61K 31/167* | (2006.01) |
| *A61K 31/5415* | (2006.01) |
| *A61K 31/7048* | (2006.01) |
| *A61K 47/34* | (2017.01) |
| *C08G 63/664* | (2006.01) |
| *A61K 31/445* | (2006.01) |
| *A61K 31/519* | (2006.01) |
| *A61K 38/12* | (2006.01) |
| *A61K 9/20* | (2006.01) |

(52) U.S. Cl.
CPC ......... *A61K 9/0024* (2013.01); *A61K 9/0019* (2013.01); *A61K 9/0029* (2013.01); *A61K 9/204* (2013.01); *A61K 9/2031* (2013.01); *A61K 31/167* (2013.01); *A61K 31/445* (2013.01); *A61K 31/519* (2013.01); *A61K 31/5415* (2013.01); *A61K 31/7048* (2013.01); *A61K 38/12* (2013.01); *A61K 47/34* (2013.01); *C08G 63/664* (2013.01)

(58) Field of Classification Search
CPC .. A61K 9/0024; A61K 9/0019; A61K 9/0029; A61K 9/2031; A61K 9/204; A61K 31/167; A61K 31/455; A61K 31/519; A61K 31/5415; A61K 31/7048; A61K 38/12; A61K 47/34; A61K 9/06; C08G 63/664; C08L 67/04
See application file for complete search history.

(56) References Cited

U.S. PATENT DOCUMENTS

| 6,350,812 | B1 | 2/2002 | Vert et al. |
| 6,541,033 | B1 | 4/2003 | Shah |
| 6,592,899 | B2 | 7/2003 | Fowers et al. |
| 9,023,897 | B2 | 5/2015 | Gaudriault |
| 2014/0113975 | A1* | 4/2014 | Shih .......... A61P 3/10 514/772.1 |
| 2015/0165042 | A1* | 6/2015 | Petit ............ A61K 47/593 424/1.85 |
| 2016/0058698 | A1 | 3/2016 | Mayadunne et al. |
| 2020/0163873 | A1* | 5/2020 | Roberge ........... C08L 67/04 |

FOREIGN PATENT DOCUMENTS

| KR | 10-2015-0025876 A | 3/2015 |
| WO | WO 01/45742 A1 | 6/2001 |
| WO | WO 01/82970 A1 | 11/2001 |
| WO | WO 02/076431 A1 | 10/2002 |
| WO | WO 2007/101443 A1 | 9/2007 |

(Continued)

OTHER PUBLICATIONS

Watt et al., Injectability as a function of viscosity and dosing materials for subcutaneous administration, International Journal of Pharmaceutics, vol. 554, pp. 376-386. (Year: 2019).*

(Continued)

*Primary Examiner* — Abigail Vanhorn
(74) *Attorney, Agent, or Firm* — Birch, Stewart, Kolasch & Birch, LLP

(57) ABSTRACT

Provided is a biodegradable drug delivery composition comprising: (i) a mixture of at least three different block copolymers, wherein each block copolymer is: (a) a biodegradable triblock copolymer having the formula: $A_v$-$B_w$-$A_x$ wherein A is a polyester and B is polyethylene glycol and v and x are from 1 to 3,000 and w is from 3 to 300 and v=x or v≠x; or (b) a biodegradable diblock copolymer having the formula: $C_y$-$A_z$ wherein A is a polyester and C is an end-capped polyethylene glycol and y=2 to 250 and z=1 to 3,000; and wherein the mixture comprises at least one (a) and at least one (b); and the weight ratio between (a) and (b) is 1:19 to 5:1; and for at least one of the copolymers according to (a) or (b) A is poly(lactic-co-glycolic acid) (PLGA); and (ii) at least one pharmaceutically active ingredient.

31 Claims, 7 Drawing Sheets

(56) References Cited

FOREIGN PATENT DOCUMENTS

WO     WO 2012/090070 A8     7/2012
WO     WO 2012/131106 A1     10/2012

OTHER PUBLICATIONS

EOR Data group, polymer properties, obtained online at: https://web.mst.edu/~weim/EORData/polymer_evaluation.html#:~:text=Polymer%20viscosity%20is%20affected%20by,viscosity%20of%20the%20polymer%20solution, downloaded on Sep. 7, 2022. (Year: 2022).*

International Search Report, issued in PCT/EP2018/069442, PCT/ISA/210, dated Oct. 23, 2018.

McKenzie et al., "Proof-of-Concept of Polymeric Sol-Gels in Multi-Drug Delivery and Intraoperative Image-Guided Surgery for Peritoneal Ovarian Cancer", Pharmaceutical Research, (2016), vol. 33, No. 9, p. 2298-2306.

Written Opinion of the International Searching Authority, issued in PCT/EP2018/063442, PCT/ISA/237, dated Oct. 23, 2018.

Yu et al., "Biodegradability and Biocompatibility of Thermoreversible Hydrogels Formed from Mixing a Sol and a Precipitate of Block Copolymers in Water", XP055513972, Biomacromolecules, (2010), vol. 11, No. 8, p. 2169-2178.

Yu et al., "Mixing a Sol and a Precipitate of Block Copolymers with Different Block Ratios Leads to an Injectable Hydrogel", XP-002586070, Biomacromolecules, (2009), vol. 10, No. 6, p. 1547-1553.

International Preliminary Report on Patentability and English translation of the Written Opinion dated Jan. 30, 2020 in PCT/EP2018/069442.

Al-Tahami et al., "Smart Polymer Based Delivery Systems for Peptides and Proteins," Recent Patents on Drug Delivery & Formulation, vol. 1, No. 1, 2007, pp. 65-71.

Hiemstra et al., "In-Situ of Biodegradable Hydrogels by Stereocomplexation of PEG-(PLLA)$_8$ and PEG-(PDLA)$_8$ Star Block Copolymers," Biomacromolecules, vol. 7, No. 10, 2006, pp. 2790-2795.

Office Action for corresponding Japanese Application No. 2020-502983, dated Jun. 14, 2022, with English translation.

Office Action for corresponding Taiwanese Application No. 107124708, dated May 3, 2022, including an English translation of the Search Report.

\* cited by examiner

○ F295: 40.00%Pol(2)_TB:DB,1:1_20.00%(75G)P2R3.5_20.00%(75G)dP0.55R6_4.00%API

△ F312: 40.00%Pol(3)_TB:DB,1:1_20.00%(75G)P2R3.5_10.00%(75G)dP0.55R6_10.00%(72CL)dP0.35R8.5_4.00%API

▽ F314: 40.00%Pol(3)_TB:DB,1:1_20.00%(75G)P2R3.5_18.00%(75G)dP0.55R6_2.00%(72CL)dP0.35R8.5_4.00%API

F295: 40.00%Pol(2)_TB:DB,1:1_20.00%(75G)P2R3.5_20.00%(75G)dP0.55R6_4.00%API

F312: 40.00%Pol(3)_TB:DB,1:1_20.00%(75G)P2R3.5_10.00%(75G)dP0.55R6_10.00%(72CL)dP0.35R8.5_4.00%API

F314: 40.00%Pol(3)_TB:DB,1:1_20.00%(75G)P2R3.5_18.00%(75G)dP0.55R6_2.00%(72CL)dP0.35R8.5_4.00%API

F285: 40.00%Pol(2)_TB:DB,1:1_20.00%P2R3.5_20.00%dP0.35R8.5_4.00%API

F295: 40.00%Pol(2)_TB:DB,1:1_20.00%(75G)P2R3.5_20.00%(75G)dP0.55R6_4.00%API

F306: 40.00%Pol(3)_TB:DB,1:1_10.00%P2R3.5_10.00%(75G)P2R3.5_20.00%dP0.35R8.5_4.00%API

F307: 40.00%Pol(3)_TB:DB,1:1_15.00%P2R3.5_5.00%(75G)P2R3.5_20.00%dP0.35R8.5_4.00%API

F308: 40.00%Pol(3)_TB:DB,1:1_18.00%P2R3.5_2.00%(75G)P2R3.5_20.00%dP0.35R8.5_4.00%API

F336: 40.00%Pol(2)_TB:DB,1:1_20.00%(75G)P2R3.5_20.00%(75G)dP0.55R6_4.00%API

F337: 40.00%Pol(3)_TB:DB,1:1_20.00%(75G)P2R3.5_10.00%(75G)dP0.55R6_10.00%(72CL)dP0.35R8.5_4.00%API

F338: 40.00%Pol(3)_TB:DB,1:1_20.00%(75G)P2R3.5_15.00%(75G)dP0.55R6_5.00%(72CL)dP0.35R8.5_4.00%API

F339: 40.00%Pol(3)_TB:DB,1:1_20.00%(75G)P2R3.5_18.00%(75G)dP0.55R6_2.00%(72CL)dP0.35R8.5_4.00%API

F336: 40.00%Pol(2)_TB:DB,1:1_20.00%(75G)P2R3.5_20.00%(75G)dP0.55R6_4.00%API

F337: 40.00%Pol(3)_TB:DB,1:1_20.00%(75G)P2R3.5_10.00%(75G)dP0.55R6_10.00%(72CL)dP0.35R8.5_4.00%API

F338: 40.00%Pol(3)_TB:DB,1:1_20.00%(75G)P2R3.5_15.00%(75G)dP0.55R6_5.00%(72CL)dP0.35R8.5_4.00%API

F339: 40.00%Pol(3)_TB:DB,1:1_20.00%(75G)P2R3.5_18.00%(75G)dP0.55R6_2.00%(72CL)dP0.35R8.5_4.00%API

BIODEGRADABLE BLOCK COPOLYMER DRUG DELIVERY COMPOSITION

CROSS REFERENCE TO RELATED APPLICATIONS

This application is the National Phase of PCT/EP2018/069442 filed on Jul. 17, 2018, which claims priority under 35 U.S.C. § 119(e) to U.S. Provisional Application No. 62/533,370 filed on Jul. 17, 2017, all of which are hereby expressly incorporated by reference into the present application.

FIELD OF THE INVENTION

The present invention relates to biodegradable drug delivery compositions comprising a mixture of at least three block copolymers taken among triblock and diblock copolymers, comprising a triblock copolymer comprising one poly(ethylene oxide) block between two polyester blocks and a diblock copolymer comprising a polyester block and an one end-capped poly(ethylene glycol), wherein for at least one of the copolymers the polyester is poly(lactic-co-glycolic acid) (PLGA) as well as at least one pharmaceutically active ingredient. The weight ratio of triblock copolymers to diblock copolymers in this formulation is 1:19 to 5:1 for modulating drug release kinetics of at least one active ingredient.

BACKGROUND OF THE PRESENT INVENTION

In the domain of sustained drug delivery, systems based on diblock or triblock copolymers have been used to deliver a variety of drugs and are generally formulated to deliver specific drugs whether they are hydrophobic drugs or hydrophilic drugs. Depending on the drug physico-chemical characteristics, the drug formulations differ in polymer concentrations, types of polymers utilized, molecular weights of the polymers and solvents used in the formulations.

Also the type of environment in which the drug is delivered is an important consideration in formulating a drug delivery system. Thus, there exist drug delivery compositions that are prepared using temperature sensitive polymers, phase sensitive polymers, pH sensitive polymers and photosensitive polymers. See, for example, K. Al-Tahami and J. Singh "Smart Polymer Based Delivery Systems for Peptide and Proteins," Recent Patents on Drug Delivery & Formulation, 1: pages: 65-71 Bentham Science Publishers, L T D. 2007.

U.S. Pat. No. 6,592,899 describes a PLA/PLGA oligomer combined with a block copolymer for enhancing the solubility of a hydrophobic drug into a hydrophilic environment.

U.S. Pat. No. 6,541,033 describes a sustained release pharmaceutical composition based on thermosensitive, biodegradable hydrogels, consisting of a block copolymer of PLA or PLGA and PEG, for the sustained delivery of biologically active agents.

Hydrogels containing triblock copolymers are described in U.S. Pat. No. 6,350,812.

U.S. Pat. No. 9,023,897 B2 describes biodegradable drug compositions comprising a triblock copolymer and a diblock copolymer and a pharmaceutically active ingredient, which is a sustained release formulation, which when altering specific triblock to diblock ratios and repeat units in the triblock and diblock, the initial burst of release of the drug is reduced and the release rate of the drug can be modulated.

However there remains a need to provide biodegradable drug delivery compositions comprising diblock and triblock copolymers with improved properties regarding the modulation of the rate of release of the at least one active ingredient. For example, it may be desirable to provide compositions with an increased rate of release of the active ingredient relative to known drug delivery compositions comprising diblock and triblock copolymers. The composition should enable the release of the at least one active ingredient to be controlled over a time period without adversely affecting the physical parameters of the formulation.

Furthermore, the biodegradable drug delivery compositions of the present invention can be formulated to be long acting formulations, which reduce the initial burst release of the drug and modulate the release rate of the drug over time according to first order or zero order or pseudo zero order kinetics. This phenomenon is illustrated in the flattening of the drug release curves.

Moreover, the biodegradable drug delivery composition can be modulated without adversely impacting the injectability of this composition.

Thus, one of the objects of the present invention is how to modulate the release kinetics of at least one pharmaceutically active ingredient from a triblock/diblock biodegradable depot without adversely impacting or by improving the physical parameters of the formulation before and/or after injection.

By "improving" means the decrease of either or both the injectability and viscosity of the formulation.

SUMMARY OF THE INVENTION

The present invention provides a biodegradable drug delivery composition comprising:
(i) a mixture of at least three different block copolymers, wherein each block copolymer is:
  (a) a biodegradable triblock copolymer having the formula:

wherein A is a polyester and B is polyethylene glycol and v and x are the number of repeat units ranging from 1 to 3,000 and w is the number of repeat units ranging from 3 to 300 and v=x or v≠x; or
  (b) a biodegradable diblock copolymer having the formula:

wherein A is a polyester and C is an end-capped polyethylene glycol and y and z are the number of repeat units with y ranging from 2 to 250 and z ranging from 1 to 3,000; and
  wherein the mixture comprises at least one (a) and at least one (b); and the weight ratio between (a) and (b) is 1:19 to 5:1; and wherein for at least one of the copolymers according to (a) or (b) A is poly(lactic-co-glycolic acid) (PLGA); and
(ii) at least one pharmaceutically active ingredient.

It has been surprisingly found that the presence of PLGA in the block copolymer mixture of the biodegradable pharmaceutical composition typically causes modulation in the rate of release of the active ingredient relative to biodegradable pharmaceutical compositions which do not comprise block copolymers comprising PLGA. This allows improved modulation of the rate of release of the at least one active ingredient.

In one embodiment of the composition, for at least one biodegradable triblock copolymer (a) A is PLGA.

In one embodiment of the composition, for at least one biodegradable diblock copolymer (b) A is PLGA.

Typically, when said polyester A is not PLGA, A is selected from the group of a polylactic acid (PLA), polyglycolic acid, polycaprolactone, poly(ε-caprolactone-co-lactide) (PCLA), polyethylene adipate, polyhydroxyalkanoate and mixtures thereof and optionally wherein the end-capped polyethylene glycol is methoxy polyethylene glycol.

In one embodiment, when said polyester A is not PLGA, A is PLA.

In one embodiment, when said polyester A is not PLGA, A is PCLA.

In one embodiment the composition further comprises at least one organic solvent. Typically the organic solvent is a pharmaceutically acceptable solvent. This organic solvent can be retained in the composition or evaporated off prior to administration.

In an embodiment of the invention provided is a biodegradable drug delivery composition as defined above which composition further comprises:

(a) a biodegradable triblock copolymer having the formula:

$$PLGA_v\text{-}PEG_w\text{-}PLGA_x$$ 

wherein v and x are the number of repeat units ranging from 1 to 3,000 and w is the number of repeat units ranging from 3 to 300 and v=x or v≠x; and/or (b) a biodegradable diblock copolymer having the formula:

$$mPEG_y\text{-}PLGA_z$$ 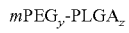

wherein y and z are the number of repeat units with y ranging from 2 to 250 and z ranging from 1 to 3,000.

In an embodiment of the invention the composition further comprises:

(a) a biodegradable triblock copolymer having the formula:

$$PCLA_v\text{-}PEG_w\text{-}PCLA_x$$ 

wherein v and x are the number of repeat units ranging from 1 to 3,000 and w is the number of repeat units ranging from 3 to 300 and v=x or v≠x; and/or (b) a biodegradable diblock copolymer having the formula:

$$mPEG_y\text{-}PCLA_z$$ 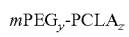

wherein y and z are the number of repeat units with y ranging from 2 to 250 and z ranging from 1 to 3,000.

In an embodiment of the invention the composition further comprises:

(a) a biodegradable triblock copolymer having the formula:

$$PLA_v\text{-}PEG_w\text{-}PLA_x$$ 

wherein v and x are the number of repeat units ranging from 1 to 3,000 and w is the number of repeat units ranging from 3 to 300 and v=x or v≠x; and/or (b) a biodegradable diblock copolymer having the formula:

$$mPEG_y\text{-}PLA_z$$ 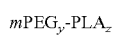

wherein y and z are the number of repeat units with y ranging from 2 to 250 and z ranging from 1 to 3,000.

Typically the composition is an injectable liquid and is suitable for forming a depot when injected into the body or are small solid particles or rod implants or spatial formulations.

Typically the mass of the polyethylene glycol chain ranges from 180 g/mol to 12 kg/mol or 194 g/mol to 12 kg/mol or 200 g/mol to 12 kg/mol or from 100 g/mol to 4 kg/mol and the molecular weight of the end-capped polyethylene glycol chain ranges from 100 g/mol to 2 kg/mol or 164 g/mol to 10 kg/mol.

The biodegradable drug delivery composition may also further comprise a pharmaceutically acceptable vehicle, such as a solvent.

In one embodiment the pharmaceutically active ingredient is hydrophobic.

In one embodiment the pharmaceutically active ingredient is meloxicam, acetaminophen or combinations thereof.

In another embodiment the at least one pharmaceutically active ingredient is present in an amount of from 0.05% to 60% (w/w %), optionally 0.05% to 40%, optionally 0.05% to 30%, optionally 0.05% to 10%, optionally 0.05% to 7%, optionally 0.05% to 2% of the total composition.

In one embodiment the biodegradable drug delivery composition is an injectable liquid and the at least one pharmaceutically active ingredient is present in an amount of 0.05% to 60% (w/w %).

In an alternative embodiment the biodegradable drug delivery composition is a rod implant and the at least one pharmaceutically active ingredient is present in an amount of from 50% to 80% (w/w %).

In a further embodiment, the copolymers are present in an amount of 2% to 60% (w/w %) of the total composition, optionally 10% to 50%, optionally 20% to 40%, optionally 20% to 35%, optionally 30% to 50%.

In one embodiment the one or more triblock copolymers are present in an amount of 1% to 50% (w/w %), optionally 5% to 40% of the total composition.

In one embodiment the one or more diblock copolymers are present in an amount of 1% to 57% (w/w %), 2.5% to 45% of the total composition.

In an additional embodiment the weight ratio of the sum of the biodegradable triblock copolymers of (a) over the sum of the biodegradable diblock copolymers of (b) in said biodegradable drug delivery composition is 1:5 to 3:1.

Typically the polyester repeat unit to ethylene oxide molar ratio in the composition is between 0.5 to 22.3, optionally 0.5 to 10, optionally 0.5 to 3.5 in the triblock and 0.8 to 15, optionally 1 to 10 in the diblock.

The composition may comprise three different block copolymers as defined above or four different block copolymers as defined above or five different block copolymers as defined above or six different block copolymers as defined above.

The composition may comprise one biodegradable triblock copolymer as defined above, or two different biodegradable triblock copolymers as defined above, or three different biodegradable triblock copolymers as defined above, or four different biodegradable triblock copolymers as defined above.

The composition may comprise one biodegradable diblock copolymer as defined above, or two different biodegradable diblock copolymers as defined above, or three different biodegradable diblock copolymers as defined above, or four different biodegradable diblock copolymers as defined above.

In one embodiment the composition comprises a triblock copolymer present in an amount of 1% to 50% (w/w %) of the total composition, a diblock copolymer present in an amount of 1% to 57% (w/w %) of the total composition, and one or more further diblock or triblock copolymers each present in an amount of 0.5 to 20 (w/w %) of the total composition.

In preferred embodiments the biodegradable drug delivery composition is a composition as defined in any of Tables 1 to 3.

Typically the release of at least one active ingredient is modulated by the composition.

In one embodiment the composition is suitable to deliver the active ingredient, optionally a therapeutically effective amount of the active ingredient, to a subject for at least 1 day, optionally at least 3 days, optionally at least 7 days, optionally at least 30 days, optionally at least 90 days, optionally at least 1 year.

In one embodiment the composition is suitable for parenteral administration.

In one embodiment the block copolymers are substantially insoluble in an aqueous solution, optionally wherein the block copolymers have less than 5%, optionally less than 1% (w/w) solubility in an aqueous solution.

In a further aspect, the present invention provides a method of modulating the kinetics of release of at least one active ingredient, said method comprising administering a biodegradable drug delivery composition as defined in any preceding claim to a subject, wherein the release kinetics of said at least one active ingredient from said biodegradable drug delivery composition are modulated without affecting one or more physical parameters of said biodegradable drug composition.

Typically the one or more physical parameters are injectability and viscosity before injection of the biodegradable drug delivery composition and depot robustness after injection of the biodegradable drug delivery composition.

F312 and F314 release kinetics are modulated compared to that of F295. The substitution of respectively 10.00% and 2.00% of (75G)dP0.55R6 initially present in F295 by the same amount of (72CL)dP0.35R8.5 induces a strong modulation of release kinetics. Indeed, the addition of a PEG-PCLA diblock copolymer as an additional biodegradable block copolymer in F295 leads to an acceleration of the release kinetics without impacting the physical parameters of F295 formulation.

Figure 2:
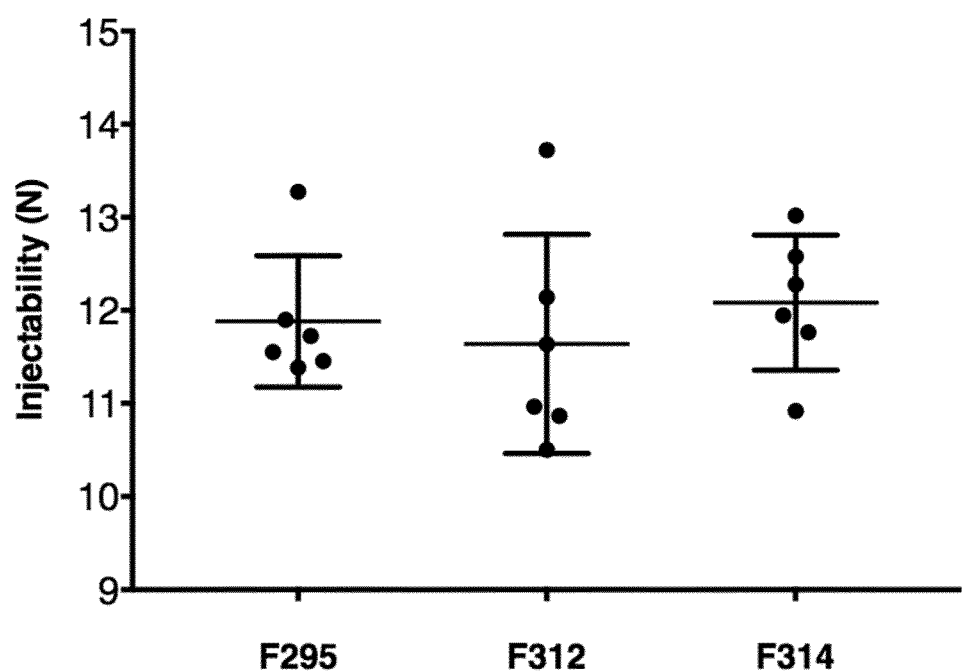

FIG. 2 is a representation of injectability values obtained from F295, F312 and F314. Data demonstrate that the addition of the additional biodegradable block copolymer does not affect the injectability of the initial formulation. Table 4 presents the details of injectability data.

Thus, results indicate that the addition of an additional biodegradable block copolymer is an efficient way to modulate the release kinetics. These results also suggest that the resulting modulatory effect is directly linked to the content of this additional biodegradable block copolymer.

Figure 3:
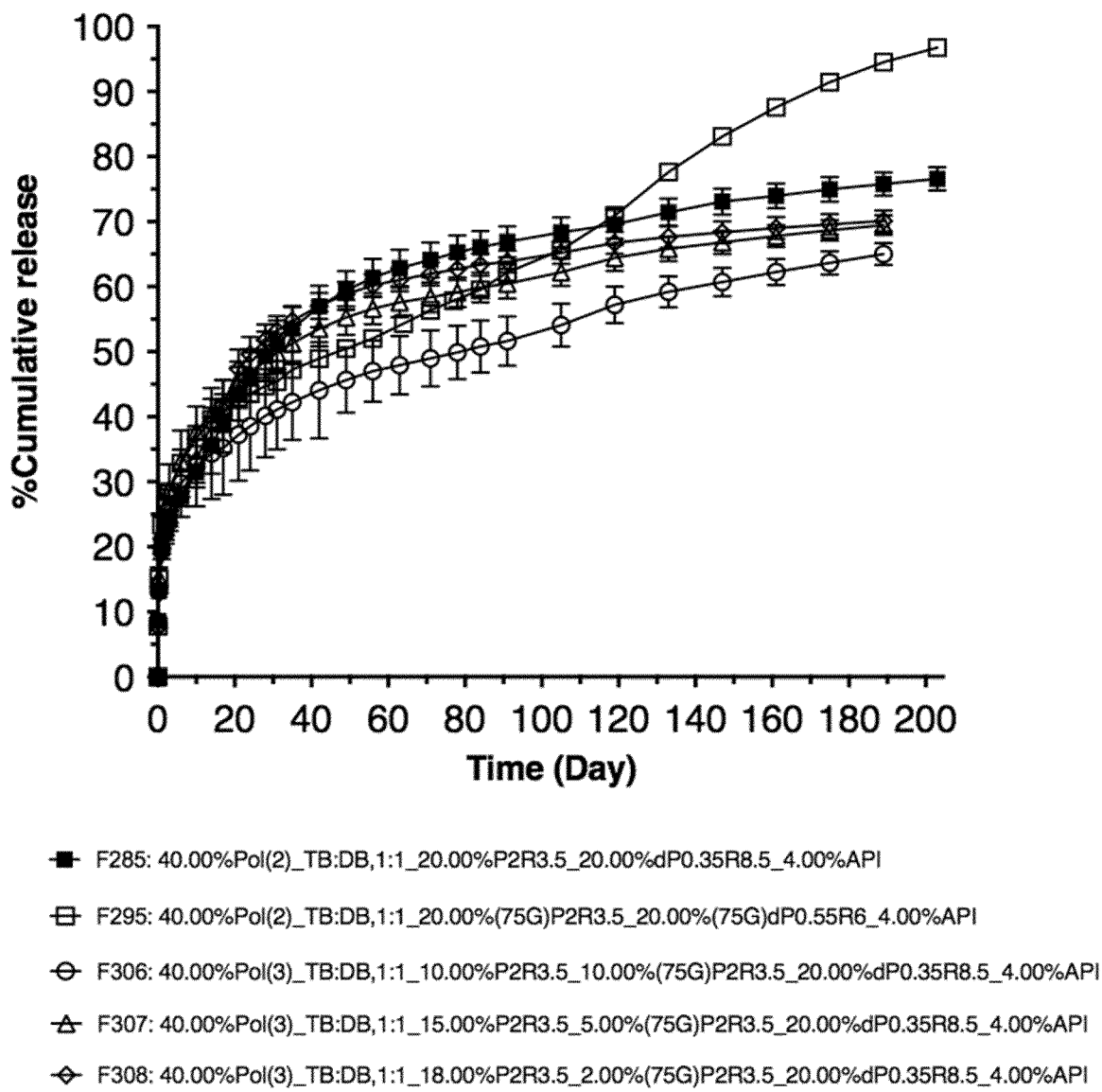

FIG. 3 displays the in vitro cumulative release of meloxicam over time from three different formulations. Formulation F285 (■) has a weight ratio of the sum of triblock to diblock of 1 containing 20.00% of P2R3.5 triblock copolymer and 20.00% of dP0.35R8.5 diblock copolymer with 4.00% active principle (API) and 56.00% of DMSO. Formulation F295 (□) has a weight ratio of the sum of triblock to diblock of 1 containing 20.00% of (75G)P2R3.5 triblock copolymer and 20.00% of (75G)dP0.55R6 diblock copolymer with 4.00% active principle (API) and 56.00% of DMSO. Formulation F306 (○) has a weight ratio of the sum of triblock to diblock of 1 containing 10.00% of P2R3.5 triblock copolymer, 10.00% of (75G)P2R3.5 and 20.00% dP0.35R8.5 diblock copolymer with 4.00% active principle (API) and 56.00% of DMSO. Formulation F307 (Δ) has a weight ratio of the sum of triblock to diblock of 1 containing 15.00% of P2R3.5 triblock copolymer, 5.00% (75G)P2R3.5 and 20.00% dP0.35R8.5 diblock copolymer with 4.00% active principle (API) and 56.00% of DMSO. Formulation F308 (◇) has a weight ratio of the sum of triblock to diblock of 1 containing 18.00% of P2R3.5 triblock copolymer, 2.00% (75G)P2R3.5 and 20.00% dP0.35R8.5 diblock copolymer with 4.00% active principle (API) and 56.00% of DMSO. The specific block copolymer formulations are set forth in Table 2 below.

F306, F307 and F308 release kinetics are modulated compared to F285 and F295 release kinetic profile. F295 formulation only contains PEG-PLGA and PLGA-PEG-PLGA copolymer. This formulation shows a non-optimal release profile with a reacceleration of the kinetics after 100 days of release. The substitution of respectively 10.00%, 5.00% and 2.00% of P2R3.5 initially present in F285 by the same amount of (75G)P2R3.5 induces a modulation of the release kinetics. Indeed, the addition of a PLGA-PEG-PLGA triblock copolymer as an additional biodegradable block copolymer in F285 leads to a proportional deceleration of the release kinetics for F306, F307 and F308 formulation without impacting the physical parameters of F285 formulation. This addition does not induce a significate reacceleration of the kinetics as observed in F295 formulation.

Figure 4:
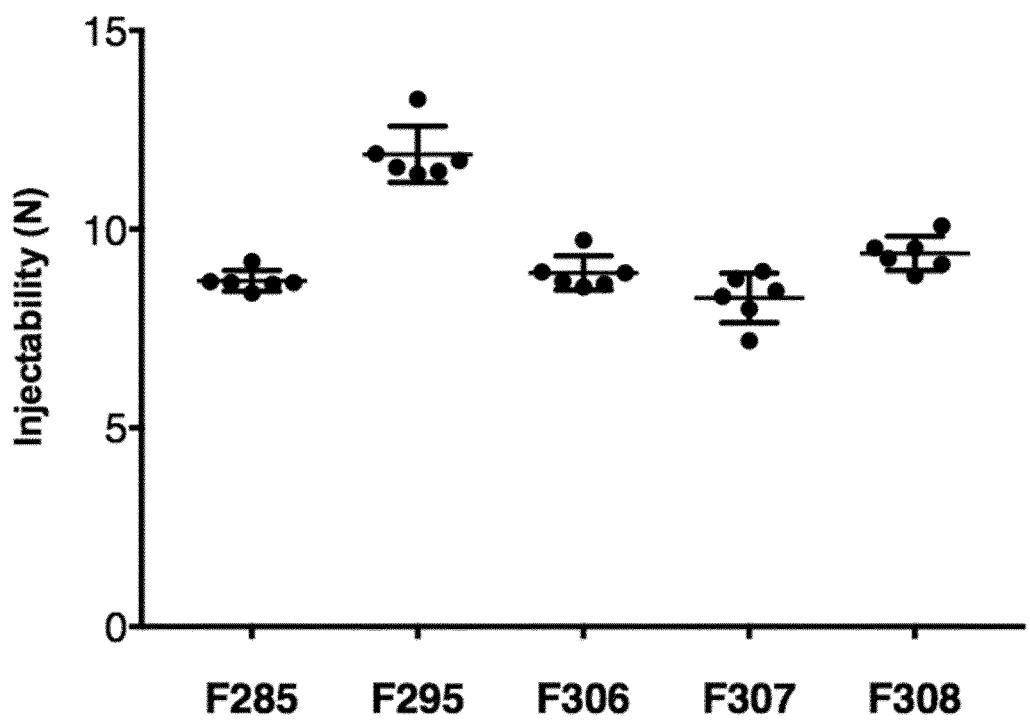

FIG. 4 is a representation of injectability values obtained from F285, F295, F306, F307 and F308

Data show that the addition of the additional biodegradable block copolymer does not affect the injectability of the initial formulation. Table 5 presents the details of injectability data.

Thus, results indicate that the addition of an additional biodegradable block copolymer is an efficient way to modulate the release kinetics. These results also suggest that the resulting modulatory effect is directly linked to the content of this additional biodegradable block copolymer.

Figure 5:
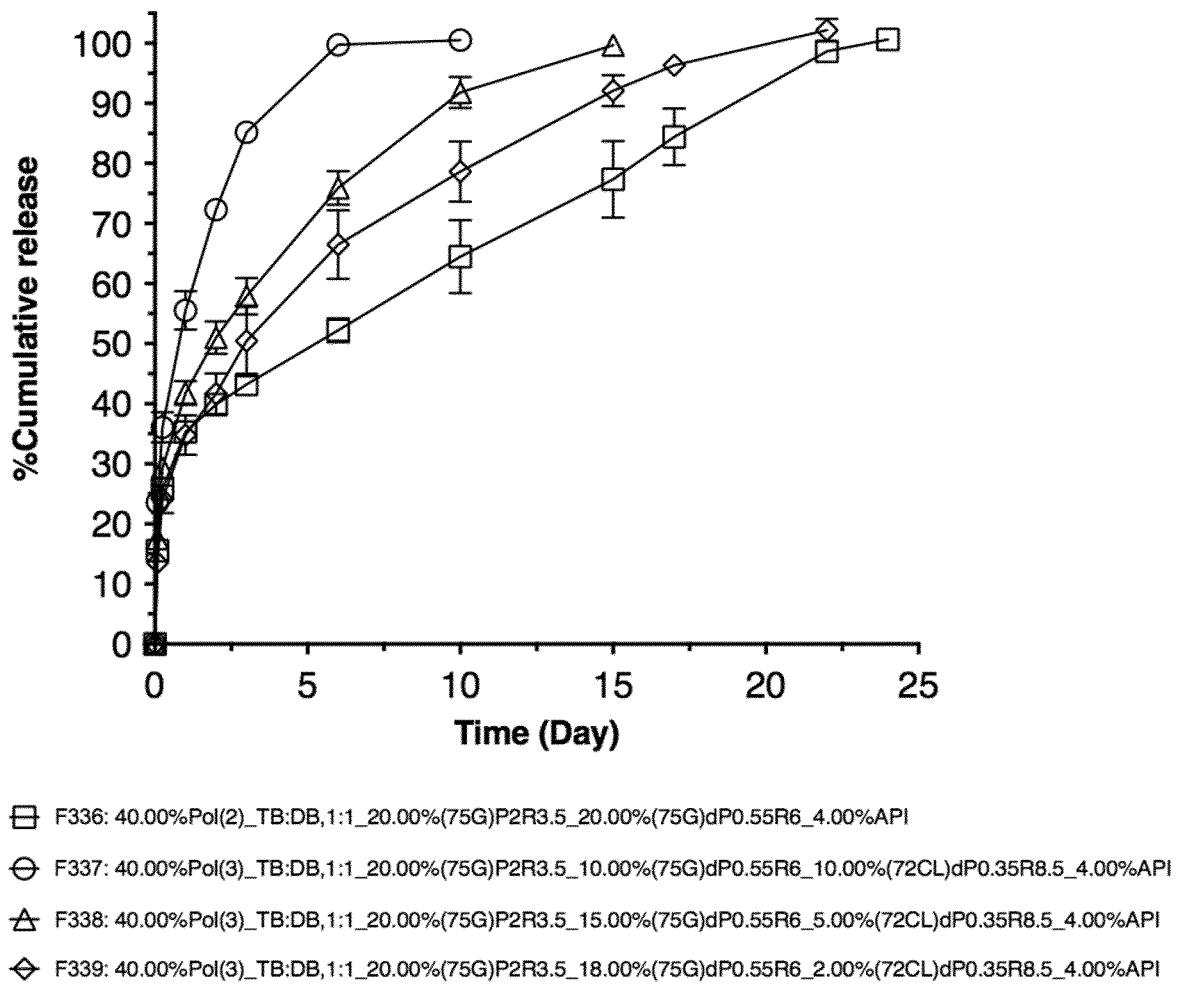

FIG. 5 displays the in vitro cumulative release of acetaminophen over time from four different formulations. Formulation F336 (□) has a weight ratio of the sum of triblock to diblock of 1 containing 20.00% of (75G)P2R3.5 triblock copolymer and 20.00% of (75G)dP0.55R6 diblock copolymer with 4.00% active principle (API) and 56.00% of DMSO. Formulation F337 (○) has a weight ratio of the sum of triblock to diblock of 1 containing 20.00% of (75G) P2R3.5 triblock copolymer, 10.00% of (75G)dP0.55R6 diblock copolymer and 10.00% of (72CL)dP0.35R8.5 diblock copolymer with 4.00% active principle (API) and 56.00% of DMSO. Formulation F338 (Δ) has a weight ratio of the sum of triblock to diblock of 1 containing 20.00% of (75G)P2R3.5 triblock copolymer, 15.00% (75G)dP0.55R6 and 5.00% (72CL)dP0.35R8.5 diblock copolymer with 4.00% active principle (API) and 56.00% of DMSO. Formulation F339 (◇) has a weight ratio of the sum of triblock to diblock of 1 containing 20.00% of (75G)P2R3.5 triblock copolymer, 18.00% (75G)dP0.55R6 and 2.00% (72CL) dP0.35R8.5 diblock copolymer with 4.00% active principle (API) and 56.00% of DMSO. The specific block copolymer formulations are set forth in Table 3 below.

Data demonstrate that the addition of different amounts of an additional biodegradable block copolymer to the initial formulation without changing its total polymer content induces a proportional modulation of the release kinetics. Indeed F337, F338, and F339 release kinetics increase gradually with higher amounts of (72CL)dP0.35R8.5 diblock copolymer. These substitutions do not impact the physical parameters of F336, the formulation being modulated.

Figure 6:
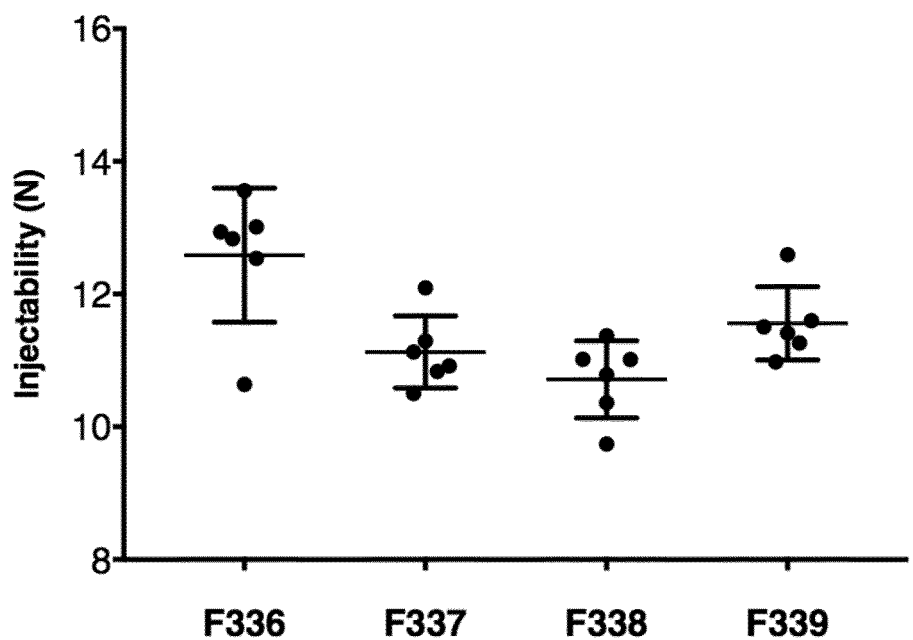

FIG. 6 shows the injectability of these compositions.

Figure 7:
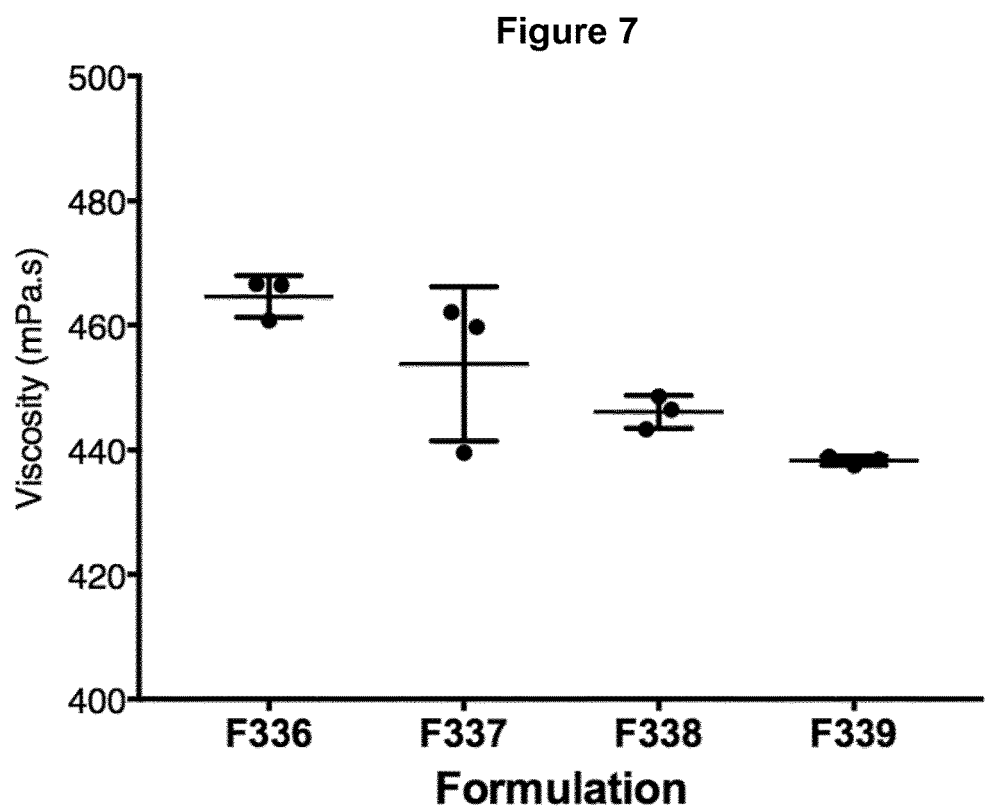

FIG. 7 is a representation of viscosity analysis measured from F336, F337, F338, and F339. Data show that the addition of the additional biodegradable block copolymer does not affect the viscosity of the initial formulation. Data represented in Table 7.

Thus, results indicate that the addition of an additional biodegradable block copolymer is an efficient way to modulate the release kinetics. These results also suggest that the resulting modulatory effect is directly linked to the content of this additional biodegradable block copolymer.

These results confirm that the addition of an additional biodegradable block copolymer is an efficient way to modulate the release kinetics without significantly changing the physical parameters of the formulation such as the injectability. These results also demonstrate that modulating the release kinetics can be highly challenging when dealing with only two block copolymers at high loading. Therefore, the addition of at least one block copolymer to the formulation can be a useful formulation tool for achieving this modulation in an efficient manner.

DESCRIPTION OF THE PREFERRED EMBODIMENTS

As used herein the term "biodegradable" means that the polyesters undergo hydrolysis to form their constituent oligomers or monomers in vivo, for example PLGA undergoes hydrolysis to form lactic acid and glycolic acid.

The term "parenteral administration" encompasses intramuscular, intraperitoneal, intra-abdominal, subcutaneous, intravenous and intraarterial. It also encompasses intradermal, intracavernous, intravitreal, intracerebral, intrathecal, epidurall and intraosseous administration.

The term "animals" encompasses all members of the Kingdom Animalia. The animal may be a human or non-human animal.

As used herein the term "plant" encompasses all members of the Plant Kingdom.

"Active ingredient" means a drug or medicine for treating or preventing various medical illnesses. For the purposes of the present application the term "active principle" has the same meaning as "active ingredient" Thus the terms active ingredient, active principle, drug or medicine are used interchangeably. The term Active Pharmaceutical Ingredient, or "API" is also used. The term drug or active ingredient as used herein includes without limitation physiologically or pharmacologically active substances that act locally or systemically in the body of an animal or plant. At least one active ingredient is present in the biodegradable drug composition of the invention.

As used herein "disease" means any disorder in a human, animal or plant caused by infection, diet, or by faulty functioning of a process.

The term "implant" means any solid object, which is formed outside the body and is placed into the body by a surgical procedure. Implants can be placed permanently or they can be removed, if necessary and depending on the circumstances. These procedures include, but are not limited to making a small cut in the body of an animal and inserting a solid or a trochar. A trochar is medical device that is made up of an obturator (which may be a metal or plastic sharpened or non-bladed tip), a cannula and a seal. The trocar functions as a portal for the subsequent placement of the implant into the body of the animal.

The term "depot injection" is an injection from a flowing pharmaceutical composition, usually subcutaneous, intradermal or intramuscular that deposits a drug in a localized mass, such as a solid mass, called a "depot". The "depots" as defined herein are in situ forming upon injection. Thus, the formulations can be prepared as liquids or micro particles and can be injected into the body.

There are several methods of injection or infusion used in humans, including intradermal, subcutaneous, intramuscular, intravenous, intraosseous, intraperitoneal, intrathecal, epidural, intracardiac, intraarticular, intracavernous, and intravitreal.

The term "spatial formulation" encompasses any formulation that can be applied on or into the animal or plant body and do not necessarily have to be administered through a syringe.

As used herein "repeat units" are the fundamental recurring units of a polymer.

By "end-capped polyethylene glycol" (cPEG) refers to PEG's in which one terminal hydroxyl group is reacted and includes alkoxy-capped PEG's, urethane-capped PEG's ester-capped PEG's and like compounds. The capping group is a chemical group which does not contain a chemical function susceptible to react with cyclic esters like lactide, glycolactide, caprolactone and the like or other esters and mixtures thereof. The reaction of an end-capped PEG polymer with lactide generates a diblock cPEG-PLA copolymer.

As used herein "polyethylene glycol", as abbreviated PEG throughout the application, is sometimes referred to as poly(ethylene oxide) or poly(oxyethylene) and the terms are used interchangeably in the present invention.

The abbreviation of "PLA" refers to poly(lactic acid).

The abbreviation of "PLGA" refers to poly(lactic-co-glycolic acid).

The abbreviation of "PCLA" refers to poly(ε-caprolactone-co-lactide).

The abbreviation "PE" refers to polyester.

The abbreviation "T" or "TB" refers to a triblock copolymer(s), while the abbreviation "D" or "DB" refers to a diblock copolymer(s).

The term "diblock" as used herein refers, for example, to an end-capped PEG-polyester coplymer. "mPEG" refers to methoxy polyethylene glycol.

The term "triblock" refers, for example, to a polyester-PEG-polyester copolymer.

The term "75G" refers to PEG-PLGA or PLGA-PEG-PLGA copolymers. The term 75G" refers to PLGA polyester based block copolymers, 75 being the LA/GA molar ratio and G referring to the presence of glycolide units.

The term "72CL" refers to PEG-PCLA or PCLA-PEG-PCLA copolymers. The term "(72)CL" refers to PCLA polyester based block copolymers 72 being the LA/CL molar ratio and CL referring to the presence of caprolactone units.

The R molar ratio refers to the number of polyester (PE) units to a number of ethylene oxide units (EO) that is present in the biodegradable drug delivery composition. For example, the number of polyester units can refer to the number of lactoyl units (LA) or the number of glycolide units (G) or the number of caprolactone units (CL) or mixtures thereof.

This R molar ratio is determined experimentally by NMR. The R molar ratio of the triblock copolymer can range from, 0.5 to 22.3, optionally 0.5 to 10, optionally 0.5 to 3.5. In another aspect the R molar ratio in the triblock can range from 0.5 to 2.5 in the biodegradable drug delivery composition described herein.

The R molar ratio in the diblock can range from 0.8 to 15, optionally 1 to 10, optionally 2 to 6, optionally from 3 to 5 in the biodegradable drug delivery composition.

The degree of polymerization or DP is the number of repeat units in an average polymer chain at time t in a polymerization reaction. For example, the degree of polymerization for PEG for the triblock is between 3 to 300 and for the diblock the degree of polymerization of PEG is between 2 to 250. For PLA, the degree of polymerization for the triblock is between 1 to 3,000 and has the same value of between 1 to 3,000 for the diblock.

As used herein "at least three" block copolymers may mean a mixture of 3, 4, 5, 6, 7, 8, 9 or 10 different block copolymers in the biodegradable drug delivery composition. In some embodiments, any combination of 3 to 10, optionally 3 to 10 triblock and diblock copolymers can be formulated, provided that at least one triblock copolymer and at least one diblock copolymer are present in the mixture, and wherein at least one diblock or triblock copolymer comprises PLGA. Other examples include 3 to 5 or 4 to 8 or 4 to 6, 3 to 7, 4 to 9 and the like mixtures of triblock and diblock copolymers can be used in the biodegradable drug compositions as described herein.

"Modulating the kinetics of the release of the at least one active ingredient" means regulating the release rate of the at least one active ingredient from the depot after it is administered in vivo. In this respect, the kinetics can be first order kinetics or pseudo-zero order kinetics depending on the formulations fabricated.

"Release modulation", as used herein, is defined as the variation of the at least one active ingredient quantity discharged over time from the depot. This required variation can be an increase or a decrease of the release from an initial kinetics, immediately or sustained long-term over the time period. Modification of the release profile may affect several periods; in the very first hours of release, for example, inducing an increase or a decrease of the initial "burst", or in more advanced periods to avoid a re-acceleration or a steep decrease of the release or for the duration of the release. Formulation modulation is a process in which particular release profiles and an optimized total release duration for a certain therapeutic application can be obtained.

As used herein, "first order kinetics" means that the process of release of the drug is directly proportional to the drug concentration involved in the process.

"Pseudo-zero order kinetics," as used herein, means that the process of the release of the drug takes place at a constant rate.

The term "physical parameters," as used herein, is intended to refer to physical properties of the composition which are important for clinical utilization of the formulations. Among them, viscosity, more specifically dynamic viscosity of the formulation, swelling and robustness of the depot after injection of the formulation are important parameters to be controlled during the optimization of the formulations. A key physical parameter of the formulations is their injectability, i.e. their suitability for administration by injection.

A depot has a "lack of robustness" if it undergoes early fragmentation into a plurality of pieces. This fragmentation can lead to unexpected and uncontrolled change of release such as burst and variability. This fragmentation is determined in the depot visually in vitro and not in viva A lack of robustness due to early physical fragmentation of the depot is distinguished from normal degradation of the polymers in the depot, for example hydrolysis of the polymers which is a key mechanism to allow release of the active ingredient, along with diffusion of the active ingredient through the pores of the polymer matrix. Preferably complete hydrolysis of the polymers forming the depot does not occur until all, or substantially all, for example 90 wt %, or 99 wt % of the active ingredient has been released from the depot.

As used herein, "swelling" is an increase in volume of the formed depot related to the water uptake. The volume of the initial depot can be increased 3 times to 5 times or 1.1 times to 3 times when injected into the body of an animal. This swelling is determined visually in vitro.

The "injectability" of a formulation, as used herein, is defined by the force needed in Newtons (N) to inject a formulation using pre-determined parameters. These parameters include: injection speed, injection volume, injection duration, syringe type or needle type and the like. These parameters may vary based on the at least one pharmaceutically active ingredient used, or the desired method of administration such as sub cutaneous, intra ocular, intra articular and the like. They will be adjusted based on the at least one pharmaceutically active ingredient present within the formulations, to be able to observe the differences and fluctuations between the formulations. The injectability must be kept low such that the formulation can be easily administered by a qualified healthcare professional in an acceptable timeframe. An ideal injectability value may be from 0.1 N to 10N with the measurement method described below. An acceptable injectability value may be from 10 N to 20 N. A non-optimal injectability may be from 20 N to 30 N. Formulations are hardly injectable from 30 to 40 N and non-injectable above 40 N. Injectability may be measured using a texturometer, preferably a Lloyd Instruments FT plus texturometer, using the following analytical conditions: 500 µL of formulation are injected through a 1 mL syringe, a 23G 1" Terumo needle with a 1 mL/min flow rate.

"Viscosity," by definition and as used herein, is a measure of a fluid's resistance to flow and gradual deformation by shear stress or tensile strength. It describes the internal friction of a moving fluid. For liquids, it corresponds to the informal concept of "thickness;" By 'dynamic viscosity" is meant a measure of the resistance to flow of a fluid under an applied force. The dynamic velocity can range from 1 mPa·s. to 3000 mPa·s or 5 mPa·s to 2500 mPa·s or 10 mPa·s to 2000 mPa·s or 20 mPa·s to 1000 mPa·s. Dynamic viscosity is determined using an Anton Paar Rheometer equipped with cone plate measuring system. Typically, 6000 µL of studied formulation are placed on the measuring plate. The temperature is controlled at +35° C. The measuring system used is a cone plate with a diameter of 50 mm and a cone angle of 1 degrees (CP50-1). The working range is from 1000 to 10 s$^{-1}$. After being vortexed for 30 seconds, formulations are placed at the center of the thermo-regulated measuring plate using a spatula. The measuring system is lowered down and a 0.104 mm gap is left between the measuring system and the measuring plate. Eleven viscosity measurement points are determined across the 1000 to 10 s$^{-1}$ shear rate range. Given values are the ones obtained at 100 s$^{-1}$.

The biodegradable triblock copolymer has the formula: $A_v$-$B_w$-$A_x$, wherein A is a polyester and B is polyethylene glycol and v and x are the number of repeat units ranging from 1 to 3,000 and w is the number of repeat units ranging from 3 to 300 and v=x or v≠x. The degree of polymerization for DP-PEG is calculated by dividing the PEG molecular weight by the EO unit molecular weight (44 g/mol). v+x equals the degree of polymerization (number of repeat units) for PLA. DP-PLA is calculated by multiplying DP-PEG by the R ratio.

However, the number of repeat units of v, w and x in the triblock composition may vary due to the targeted time of release of the active ingredient and the type of active ingredient itself. Therefore the number of repeat units in the triblock of v, w and x can range from 1 to 3,300 or from 60 to 2,800 or from 300 to 1,700 or from 500 to 1, 250 and v=x or v≠x. For instance, w can be 273, while v+x can be 682 and v≠x or w can be 136 and v+x can be 272 and v=x or w can be 45.5 and v+x can be 546 or w can be 273 and v+x can be 136.

The molecular weight of the PEG in the triblock can range from 180 g/mol to 12,000 g/mol.

At least one of the block copolymers in the composition (diblock and/or triblock) must comprise PLGA as the polyester.

When the polyester in the triblock is not PLGA, the polyester in the triblock can be polylactic acid (PLA), poly(ε-caprolactone-co-lactide) (PCLA), polycaprolactone (PCL), polyethylene adipate (PEA), polyglycolic acid (PGA), polyhydroxyalkanoate (PHA) or mixtures thereof. In one embodiment the polyester that is used is polylactic acid. In another embodiment the polyester is poly(ε-caprolactone-co-lactide) (PCLA).

The biodegradable triblock copolymers are then combined with the biodegradable diblock copolymers having the formula: $C_y$-$A_z$, wherein A is a polyester and C is an end-capped polyethylene glycol and y and z are the number of repeat units with y ranging from 1 to 3,000 and z ranging from 1 to 300. This combination has a weight ratio of the sum of triblock copolymer to diblock copolymer ranging from 1:19 to 5:1.

Examples of end-capped polyethylene glycols include alkoxy capped PEG's such as methoxyPEG or ethoxyPEG, urethane-capped PEG's, ester-capped PEG's, amine-capped PEG's and amide-capped PEG's. This list of end-capped PEG's is not exhaustive and a person skilled in the art would recognize additional end-capped PEG's, which are not listed.

Moreover, the number of repeat units (degree of polymerization (DP)) of y and z in the diblock composition may also vary. Thus, y can, for example, range from 8 to 500 or 150 to 850 or 200 to 500 or 30 to 1,200 and z can range from 32 to 123 or 7 to 250. For example, y be 32. The degree of polymerization for DP-PEG is calculated by dividing the PEG molecular weight of the capped PEG by the EO unit molecular weight (44 Da). The DP-PLA is calculated by multiplying DP-PEG by the R ratio.

When the polyester in the diblock is not PLGA, the polyester in the diblock can be polylactic acid (PLA), poly(ε-caprolactone-co-lactide) (PCLA), polycaprolactone (PCL), polyethylene adipate (PEA), polyglycolic acid (PGA), or polyhydroxyalkanoate (PHA) or mixtures thereof (PGA), or polyhydroxyalkanoate (PHA) or mixtures thereof. In one embodiment the polyester that is used is polylactic acid. In another embodiment the polyester is poly(ε-caprolactone-co-lactide) (PCLA)

The at least three block copolymer(s) are combined by dissolving them together at room temperature in a pharmaceutically acceptable solvent. They are combined such that these at least three block copolymers are in a final concentration of 2% to 60% (w/w %) of the total composition or optionally 10% to 50%, optionally 20% to 40%, optionally 20% to 35%, optionally 30% to 50% of the total composition. In one aspect the pharmaceutically acceptable solvent is an organic solvent. This organic solvent can be retained in the composition or evaporated off prior to administration.

A "small quantity," as used herein, is defined as an amount of copolymer lower than the combined amount of the other two block copolymers in the biodegradable drug composition. This small quantity of the at least one additional biodegradable block copolymer is not an addition to the total polymer content but added as an addition of a substitute block copolymer from the existing classical two block copolymer composition. This addition of an at least one additional biodegradable block copolymer to the formulation composition, without changing either the total amount of block copolymers within the formulation or the TB/DB ratio, is an appropriate way to modify the release profile without affecting relevant physical parameters. For example, the at least one additional biodegradable block copolymer can be less than 25% of the total block copolymer content or can be, for example, less than 5%. In another aspect a 'small quantity' can range from 1% to 25% of the total block copolymer content or 2.5% to 15% of the total block copolymer content or 3.5% to 12% of the total block copolymer content.

The present invention relates to the modulation of the release kinetics of at least one active ingredient from a triblock/diblock biodegradable pharmaceutical composition without adversely impacting critical formulation characteristics, including physical parameters such as robustness of the depot, or injectability or viscosity of the formulation. The presence of a triblock or diblock copolymer comprising PLGA as an additional biodegradable block copolymer to the initial TB/DB mixture allows tuning of the release kinetics without impacting the injectability, which if not, may prevent the compositions from being injectable through standard devices.

The presence of PLGA in the block copolymer mixture of the biodegradable pharmaceutical composition typically causes modulation of the rate of release of the active ingredients relative to biodegradable pharmaceutical compositions which do not comprise block copolymers comprising PLGA.

The combination of at least three block copolymers as defined in claim 1 substantially amplifies the range of attainable release of the at least one active ingredient and does so in a more efficient modulating manner.

This formulation allows modulation of the release profile of the at least one active ingredient inducing an increase or a decrease of the release kinetic over time without significantly impacting the physical parameters of the initial formulation. The total polymer content as well as the total of at least one active ingredient content of the formulation is still unchanged and gives to the formulation the same relevant parameters such as injectability or depot robustness. The goal of this approach is to modify the release kinetics keeping the benefits provided by the initial triblock and diblock PEG-PLA copolymer (injectability, depot robustness etc.)

The mixtures of at least three triblock copolymers and diblock copolymers can contain any polyester, provided that at least one of the block copolymers comprises PLGA, such as polylactic acid (PLA), poly(ε-caprolactone-co-lactide) (PCLA), polycaprolactone (PCL), polyethylene adipate (PEA), polyglycolic acid (PGA), polyhydroxyalkanoate (PHA) and mixtures thereof. Thus, the triblock can contain, for example, PCL-PEG-PCL or PEA-PEG-PEA or PGA-PEG-PGA or PHA-PEG-PHA or PLA-PEG-PLA or PLA-PEG-PCL, $PCL_y$-$PEG_w$-$PCLA_x$ or PHA-PEG-PEA. The diblock can contain, for example, end-capped PEG-PLA or end-capped PEG-PCL or end-capped PEG-PEA or end-capped PEG-PGA or end-capped PEG-PLGA or end-capped PEG-PHA or end-capped PEG-PCLA.

The weight ratio of the sum of the biodegradable triblock copolymer and the biodegradable diblock copolymer in the biodegradable drug delivery composition is from 1:19 to 5:1, optionally from 1:5 to 3:1, optionally from 1:2 to 3:1. Therefore this ratio can be, for example, 1:5, 1:10, 1:19, 4:1, 3:1 or 2:1.

The length of the polyester chain is defined by its polyester to ethylene oxide molar ratio, which is between 0.5 to 22.3, optionally 0.5 to 10, optionally 0.5 to 3.5, optionally 0.5 to 2.5 or for the triblock copolymer and 0.8 to 15, optionally 0.8 to 13, optionally 1 to 10, optionally 3 to 5, optionally 2 to 6 for the diblock copolymer. Thus, for example, if polylactic acid is used the chain length is defined by the lactic acid/ethylene oxide molar ratio. Similarly if polyglycolic acid is used, the chain length is defined by the polyglycolic acid/ethylene oxide molar ratio or the polycaprolactone/ethylene oxide molar ratio or the polyhydroxyalkanoate/ethylene oxide molar ratio. If poly(lactic-co-glycolic) acid is used the chain length is defined by the R ratio.

The weight of the end-capped polyethylene glycol can range from 120 g/mol to 10,000 g/mol or 164 g/mol to 2,000 g/mol or from 100 g/mol to 2 kg/mol or from 200 g/mol to 8,000 g/mol or from 194 g/mol to 7,500 g/mol or from 100 g/mol to 6,500 g/mol or from 164 g/mol to 9,500 g/mol. It can range in the lower 130 to 300 g/mol range or in the 125 g/mol to 800 g/mol range.

The molecular weight of the polyethylene glycol chain ranges from 180 g/mol to 12 kg/mol in the biodegradable drug delivery composition or it can range from 400 g/mol to 12 kg/mol or 194 g/mol to 12 kg/mol.

The polymer total amount is in a range from 2% to 60% (w/w %), optionally 1% to 50% (w/w %), optionally 10% to 50%, optionally 20% to 40%, optionally 20% to 35%, optionally 30% to 50% of the total weight of the composition. In another embodiment the total weight of the polymers present in the biodegradable drug composition is 30% to 50% (w/w %) or 10% to 35% (w/w %) of the total weight of the composition. In yet another embodiment the polymers are present in the biodegradable drug composition at 40% to 50% (w/w %) or 20% to 45% (w/wt %) of the total weight of the composition.

Thus, the triblock copolymer is present in an amount of 1% to 50% (w/w %) or 3% to 45% (w/w %) of the total weight of the composition. In another aspect the triblock copolymer is present in an amount of 6% to 10% (w/w %) of the total weight of the composition. In yet another aspect the triblock copolymer is present in an amount of 20% to 40% (w/w %) of the total weight of the composition. In yet another aspect the triblock is present in an amount of 5% to 40% (w/w %) of the total composition.

Likewise the diblock copolymer can be present in the biodegradable drug composition in an amount of 1% to 57% (w/w %) of the total weight of the composition. In another aspect the diblock copolymer is present in an amount of 2.5% to 45% (w/w %) of the total weight of the composition. In yet another aspect the diblock copolymer is present in an amount of 5% to 40% (w/w %) of the total weight of the composition. In yet another aspect the diblock is present in an amount of 8% to 20% (w/w %) of the total composition.

The third or further biodegradable block copolymer may be present in the biodegradable drug composition in an amount of at least 0.5% to 20% (w/w %) of the total composition. In another example, it can be present in a range of 1% to 10% (w/wt %); in yet another it can be in the range of 2% to 8% (w/w %) of the total composition. In yet another aspect, the at least one additional biodegradable block copolymer can be present in an amount of 3% to 5% (w/w %) of the total composition.

The at least one pharmaceutically active ingredient is entrapped in the mixture of the at least three triblock and diblock biodegradable drug delivery compositions. Representative drugs and biologically active agents to be used in the invention include, without limitation, peptide drugs, protein drugs, desensitizing agents, antigens, vaccines, vaccine antigens, anti-infectives, antidepressants, stimulants, opiates, antipsychotics, atypical antipsychotics, glaucoma medications, antianxiety drugs, antiarrhythmics, antibacterials, anticoagulents, anticonvulsants, antidepressants, antimetics, antifungals, antineoplastics, antivirals, antibiotics, antimicrobials, antiallergenics, anti-diabetics, steroidal antiinflammatory agents, decongestants, miotics, anticholinergics, sympathomimetics, sedatives, hypnotics, psychic energizers, tranquilizers, androgenic steroids, estrogens, progestational agents, humoral agents, prostaglandins, analgesics, corticosteroids, antispasmodics, antimalarials, antihistamines, cardioactive agents, non-steroidal anti-inflammatory agents, antiparkinsonian agents, antihypertensive agents, beta-adrenergic blocking agents, nutritional agents, gonadotrophin releasing hormone agonists, insecticides, anti-helminthic agents or combinations thereof.

The pharmaceutically active ingredient may be meloxicam, acetaminophen or combinations thereof.

Combinations of drugs can be used in the biodegradable drug delivery composition of this invention. For instance, if one needs to treat Lupus erythematosis, non-steroidal antiinflammatory agents and corticosteroids can be administered together in the present invention.

Veterinary medicaments such as medicines for the treatment of worms or vaccines for animals are also part of the present invention.

Viral medicaments for plants such as those viruses from Potyviridae, Geminiviridae, the *Tospovirus* genus of Bunyaviridiae and Banana streak virus are also encompassed by the present invention. Also medicaments for tobacco mosaic virus, turnip crinkle, barley yellow dwarf, ring spot watermelon and cucumber mosaic virus can be used in the biodegradable drug delivery composition of the invention.

To those skilled in the art, other drugs or biologically active agents that can be released in an aqueous environment can be utilized in the described delivery system. Also, various forms of the drugs or biologically active agents may be used. These include without limitation forms such as uncharged molecules, molecular complexes, salts, ethers, esters, amides, etc., which are biologically activated when injected into the animal or plant or used as a spatial formulation such that it can be applied on or inside the body of an animal or plant or as a rod implant.

The pharmaceutically effective amount of an active ingredient may vary depending on the active ingredient, the extent of the animal's or plants medical condition and the time required to deliver the active ingredient. There is no critical upper limit on the amount of active ingredient incorporated into the polymer solution except for that of an acceptable solution or dispersion viscosity for injection through a syringe needle and that it can effectively treat the medical condition without subjecting the animal or plant to an overdose. The lower limit of the active ingredient incorporated into the delivery system is dependent simply upon the activity of the active ingredient and the length of time needed for treatment.

Generally the pharmaceutically active ingredient is present in an amount of 0.05% to 60% (w/w %) of the total weight of the composition. In another aspect the active ingredient is present in 1% to 40% (w/w %) of the total weight of the composition. In another aspect the active ingredient is present in 2% to 4% (w/w %) of the total weight of the composition. In yet another aspect the active ingredient, which is a small molecule, is present in an amount of 1% to 20% (w/w %) of the total weight of the composition.

In the biodegradable drug delivery composition of the present invention, the pharmaceutically effective amount can be released gradually over an extended period of time. This slow release can be continuous or discontinuous, linear or non-linear and can vary due to the composition of the triblock copolymer and diblock copolymer.

The active ingredient can be released for a duration of between 1 day to 1 year or longer depending upon the type of treatment needed and the biodegradable drug delivery composition used. In one embodiment the biodegradable drug delivery composition can deliver the active ingredient for at least 1 day, optionally at least 3 days, optionally at least 7 days. In another embodiment the biodegradable drug delivery composition can deliver the active ingredient for at least 30 days. In one embodiment the biodegradable drug delivery composition can deliver the active ingredient for at least 90 days. In yet another embodiment the biodegradable drug delivery composition can deliver an active ingredient for 1 year or longer.

The biodegradable drug delivery composition can be an injectable liquid, preferably at room temperature, and can be injected through a syringe without excessive force. These biodegradable drug delivery compositions are also in situ forming and biodegradable and turn into solid depots when injected into the animal or plant. It can also be prepared as microparticles that can be injected via a syringe.

Alternatively, the biodegradable drug composition is produced as a solid, prepared as small particles (that are not injectable due to their size) and prepared as a powder which is sprinkled on the injured site. The solid implants can be formulated in any shape that I desirable for its application into the body.

In another embodiment the drug delivery composition is a rod implant, which can be implanted under the skin or in another compartment in the body. In another aspect the drug delivery composition can be prepared and applied as a film. In yet another aspect the biodegradable drug delivery composition can be used as a spatial formulation such that it can be applied onto or inside the body of an animal or plant. It can be applied anywhere on the body, including in the eye.

The biodegradable drug delivery composition can further comprise a pharmaceutically acceptable carrier, adjuvant or vehicle. An acceptable carrier can be saline, buffered saline and the like. It can be added to the biodegradable drug delivery composition after its formulation with the drug and a mixture of at least three copolymers taken among triblock copolymers and diblock copolymers.

The adjuvant can be formulated simultaneously when mixing the drug. In this regard the adjuvants that can be used are alum, aluminum phosphate, calcium phosphate, MPL™, CpG motifs, modified toxins, saponins, endogenous stimulatory adjuvants such as cytokines, Freunds complete and incomplete adjuvants, ISCOM type adjuvants, muramyl peptides and the like.

The vehicle can be any diluent, additional solvent, filler or binder that may alter the delivery of the active ingredient when needed in the biodegradable drug delivery composition. Examples include small amounts of triglycerides such as triacetin or tripropionin. The amount that can be used in the present biodegradable drug delivery compositions of the present invention can vary from 12% to 20% (w/w %). In one aspect a triacetin can be added in the formulation at 17% (w/w %). In another aspect tripropionin (abbreviated herein as Tripro) can be added at 16% (w/w %).

In one embodiment the composition may comprise an organic solvent. The organic solvent may be selected from the group of: benzyl alcohol, benzyl benzoate, dimethyl isosorbide (DMI), dimethyl sulfoxide (DMSO), ethyl acetate, ethyl benzoate, ethyl lactate, glycerol formal, methyl ethyl ketone, methyl isobutyl ketone, N-ethyl-2-pyrrolidone, N-methyl-2-pyrrolidinone(NMP), pyrrolidone-2, tetraglycol, triacetin, tributyrin tripropionin (tripro) and mixtures thereof. In one embodiment DMSO, NMP, tripro or mixtures thereof can be used as solvents.

In a further aspect, provided is a method for preparing the biodegradable drug delivery composition comprising a mixture of at least three block copolymers taken among triblock copolymers and diblock copolymers is also encompassed by the invention. This method comprises:
  (i) dissolving in an organic solvent a mixture of at least three triblock and diblock copolymers comprising:
  (a) a biodegradable triblock copolymer having the formula:

$A_v\text{-}B_w\text{-}A_x$ wherein A is a polyester and B is polyethylene glycol and v and x are the number of repeat units ranging from 1 to 3,000 and w is the number of repeat units ranging from 3 to 300 and v=x or v≠x; or
  (b) a biodegradable diblock copolymer having the formula:

$C_y\text{-}A_z$ wherein A is a polyester and C is an end-capped polyethylene glycol and y and z are the number of repeat units with y ranging from 2 to 250 and z ranging from 1 to 3,000; and
  wherein the mixture comprises at least one (a) and at least one (b); and the weight ratio between (a) and (b) is 1:19 to 5:1; and wherein for at least one of the copolymers according to (a) or (b) A is poly(lactic-co-glycolic acid) (PLGA);
  (ii) adding at least one pharmaceutically active ingredient to said polymer mixture.

In this method, combinations of at least three block copolymers comprising at least one diblock and at least one triblock, for example 3 to 10 block copolymers can be formulated, provided that at least one bock copolymer comprises PLGA. For instance, two triblock copolymers can be combined with one diblock or one triblock copolymer can be combined with two diblocks. Five triblock copolymers can be combined with five diblocks or three triblock copolymers can be combined with seven diblock copolymers. Four triblocks can be combined with three diblocks and the like.

The polyester in the triblock can be polylactic acid (PLA), polycaprolactone (PCL), poly(ε-caprolactone-co-lactide) (PCLA), polyethylene adipate (PEA), polyglycolic acid (PGA), poly(lactic-co-glycolic acid) (PLGA), polyhydroxyalkanoate (PHA) and mixtures thereof. In one embodiment the polyester that is used is polylactic acid.

The polyester in the diblock can be polylactic acid (PLA), polycaprolactone (PCL), poly(ε-caprolactone-co-lactide) (PCLA), polyethylene adipate (PEA), polyglycolic acid (PGA), poly(lactic-co-glycolic acid) (PLGA) or polyhydroxyalkanoate (PHA) and mixtures thereof. In one embodiment the polyester that is used is polylactic acid. In another embodiment the polyester is poly(lactic-co-glycolic acid).

The organic solvent that can be used in the method described herein may be selected from the group of: benzyl alcohol, benzyl benzoate, dimethyl isosorbide (DMI), dimethyl sulfoxide (DMSO), ethyl acetate, ethyl benzoate, ethyl lactate, glycerol formal, methyl ethyl ketone, methyl isobutyl ketone, N-ethyl-2-pyrrolidone, N-methyl-2-pyrrolidinone(NMP), pyrrolidone-2, tetraglycol, triacetin, tributyrin, tripropionin (tripro), and mixtures thereof. In one embodiment DMSO, NMP, tripro or mixtures thereof can be used as solvents.

The organic solvent is typically present in an amount of 35% to 75% (w/w %) of the total composition. In another aspect the organic solvent used in the preparation of the biodegradable drug delivery composition is present in an amount of 50% to 60% (w/w %) of the total composition. In yet another aspect the solvent used in the preparation of the biodegradable drug delivery composition is present in an amount of 25% to 90% (w/w %) of the total composition. The amount of organic solvent in another embodiment can be 0% if it is evaporated.

This organic solvent can be retained in the composition or evaporated off prior to administration.

Some mPEG-OH may be contaminated with a small amount of OH-PEG-OH. By following the methods of the present invention and using the contaminated mPEG-OH the final product may be mPEG-PLA contaminated with a small amount of PLA-PEG-PLA, which is encompassed by the present invention.

In an additional aspect, the present invention provides a method of modulating the kinetics of release of at least one active ingredient said method comprising administering a biodegradable drug delivery composition comprising:
(i) a mixture of at least three different block copolymers, wherein each block copolymer is:
  (a) a biodegradable triblock copolymer having the formula:

wherein A is a polyester and B is polyethylene glycol and v and x are the number of repeat units ranging from 1 to 3,000 and w is the number of repeat units ranging from 3 to 300 and v=x or v≠x; or
  (b) a biodegradable diblock copolymer having the formula:

wherein A is a polyester and C is an end-capped polyethylene glycol and y and z are the number of repeat units with y ranging from 2 to 250 and z ranging from 1 to 3,000; and
  wherein the mixture comprises at least one (a) and at least one (b); and the weight ratio between (a) and (b) is 1:19 to 5:1; and wherein for at least one of the copolymers according to (a) or (b) A is poly(lactic-co-glycolic acid) (PLGA); and
(b) at least one pharmaceutically active ingredient.

In this method of modulating the kinetics of release of at least one active ingredient the polyester in the triblock and diblock can be selected from the group of a polylactic acid, polyglycolic acid, polycaprolactone, poly(ε-caprolactone-co-lactide), polyethylene adipate, poly(lactide-co-glycolide) acid, polyhydroxyalkanoate and mixtures thereof and the end-capped polyethylene glycol can be methoxy polyethylene glycol.

In this method of modulating the kinetics of release of at least one active ingredient the molecular weight of the polyethylene glycol chain can range from 180 g/mol to 12 kg/mol or 194 g/mol to 12 kg/mol and the molecular weight of the end-capped polyethylene glycol chain ranges from 100 g/mol to 4 kg/mol or 164 g/mol to 10 kg/mol.

In another embodiment of the method the at least one pharmaceutically active ingredient used in the method is present in an amount of from 0.05% to 60% (w/w %), optionally 0.05% to 40%, optionally 0.05% to 30%, optionally 0.05% to 10%, optionally 0.05% to 7%, optionally 0.05% to 2% of the total composition.

In one embodiment of the method the biodegradable drug delivery composition is an injectable liquid and the at least one pharmaceutically active ingredient is present in an amount of 0.05% to 60% (w/w %).

In an alternative embodiment of the method the biodegradable drug delivery composition is a rod implant and the at least one pharmaceutically active ingredient is present in an amount of from 50% to 80% (w/w %).

In a further embodiment of the method, the copolymers are present in an amount of 2% to 60% (w/w %) of the total composition, optionally 10% to 50%, optionally 20% to 40%, optionally 20% to 35%, optionally 30% to 50%.

In one embodiment of the method the one or more triblock copolymers are present in an amount of 1% to 50% (w/w %), optionally 5% to 40% of the total composition.

In one embodiment of the method the one or more diblock copolymers are present in an amount of 1% to 57% (w/w %), 2.5% to 45% of the total composition.

In an additional embodiment of the method the weight ratio of the sum of the biodegradable triblock copolymers of (a) over the sum of the biodegradable diblock copolymers of (b) in said biodegradable drug delivery composition is 1:5 to 3:1.

Typically the polyester repeat unit to ethylene oxide molar ratio in the composition used in the method is between 0.5 to 22.3, optionally 0.5 to 10, optionally 0.5 to 3.5 in the triblock and 0.8 to 15, optionally 1 to 10 in the diblock.

In the method, as described herein, of modulating the kinetics of release of at least one active ingredient, the composition can be an injectable liquid or microparticles and form a depot when injected into the body or a solid or are small solid particles or rod implants or spatial formulations that can be formulated as solids and placed into the body using a trocar, for example.

Use of the biodegradable drug delivery composition, as described herein, to modulate the kinetics of release of at least one active ingredient is another aspect of the invention.

The present invention provides a drug delivery composition comprising:
(i) a mixture of at least three different block copolymers, wherein each block copolymer is:
  (a) a triblock copolymer having the formula:

$A_v\text{-}B_w\text{-}A_x$ wherein A is a polyester and B is polyethylene glycol and v and x are the number of repeat units ranging from 1 to 3,000 and w is the number of repeat units ranging from 3 to 300 and v=x or v≠x; or
  (b) a diblock copolymer having the formula:

$C_y\text{-}A_z$ wherein A is a polyester and C is an end-capped polyethylene glycol and y and z are the number of repeat units with y ranging from 2 to 250 and z ranging from 1 to 3,000; and
  wherein the mixture comprises at least one (a) and at least one (b); and the weight ratio between (a) and (b) is 1:19 to 5:1; and wherein for at least one of the copolymers according to (a) or (b) A is poly(lactic-co-glycolic acid) (PLGA); and
(ii) at least one pharmaceutically active ingredient.

The present invention further provides a method of modulating the kinetics of release of at least one active ingredient, said method comprising administering a drug delivery composition as defined in any preceding claim to a subject, wherein the release kinetics of said at least one active ingredient from said drug delivery composition are modulated without affecting one or more physical parameters of said biodegradable drug delivery composition.

The present invention further provides use of the biodegradable drug delivery composition as defined above to modulate the kinetics of release of at least one active ingredient.

A number of embodiments and/or aspects of the invention have been described. Nevertheless, it will be understood that various modifications may be made without departing from the spirit and scope of the invention.

Other aspects and embodiments are set forth below, or will readily arise from the following description of the preferred embodiments.

Described is a biodegradable drug delivery composition comprising a mixture of at least three triblock copolymers and diblock copolymers comprising:
(a) a biodegradable triblock copolymer having the formula:

$A_v\text{-}B_w\text{-}A_x$ wherein A is a polyester and B is polyethylene glycol and v and x are the number of repeat units ranging from 1 to 3,000 and w is the number of repeat units ranging from 3 to 300 and v=x or v≠x;
(b) a biodegradable diblock copolymer having the formula:

$C_y\text{-}A_z$ wherein A is a polyester and C is an end-capped polyethylene glycol and y and z are the number of repeat units with y ranging from 2 to 250 and z ranging from 1 to 3,000, wherein the weight ratio of the sum of the biodegradable triblock copolymer of (a) and the biodegradable CA diblock copolymer of (b) is 1:19 to 5:1 in said biodegradable drug composition;
(c) at least one additional biodegradable block copolymer; and
(d) at least one pharmaceutically active principle, wherein the release kinetics of said at least one active principle from said biodegradable drug delivery composition is modulated without affecting physical parameters of said biodegradable drug composition.

Described is a biodegradable drug delivery composition comprising a mixture of at least three triblock copolymers and diblock copolymers comprising:
(a) a biodegradable triblock copolymer having the formula:

$A_v\text{-}B_w\text{-}A_x$ wherein A is a polyester and B is polyethylene glycol and v and x are the number of repeat units ranging from 1 to 3,000 and w is the number of repeat units ranging from 3 to 300, v and x being ester repeat units and w being ethylene oxide repeat units and v=x or v≠x;
(b) a biodegradable diblock copolymer having the formula:

$C_y\text{-}A_z$ wherein A is a polyester and C is an end-capped polyethylene glycol and y and z are the number of repeat units with y ranging from 2 to 250 and z ranging from 1 to 3,000, y being the number of ethylene oxide repeat units and z the number of ester repeat units wherein the weight ratio of the sum of the biodegradable triblock copolymer of (a) and the biodegradable CA diblock copolymer of (b) is 1:19 to 5:1 in said biodegradable drug composition;
(c) at least one additional biodegradable block copolymer; and
(d) at least one pharmaceutically active principle, wherein the release kinetics of said at least one active principle from said biodegradable drug delivery composition is modulated without affecting physical parameters of said biodegradable drug composition.

Described is a biodegradable drug delivery composition comprising a mixture of at least three triblock copolymers and diblock copolymers comprising:
(a) a biodegradable triblock copolymer having the formula:

$PLGA_v\text{-}PEG_w\text{-}PLGA_x$ wherein v and x are the number of repeat units ranging from 1 to 3,000 and w is the number of repeat units ranging from 3 to 300 and v=x or v≠x;
(b) a biodegradable diblock copolymer having the formula:

$mPEG_y\text{-}PLGA_z$ wherein y and z are the number of repeat units with y ranging from 2 to 250 and z ranging from 1 to 3,000, wherein the weight ratio of the sum of the biodegradable triblock copolymer of (a) and the biodegradable diblock copolymer of (b) is 1:19 to 5:1 in said biodegradable drug composition;
(c) at least one additional biodegradable block copolymer; and
(d) at least one pharmaceutically active principle, wherein the release kinetics of said at least one active principle from said biodegradable drug delivery composition is modulated without affecting physical parameters of said biodegradable drug composition.

Described is a biodegradable drug delivery composition comprising a mixture of at least three triblock copolymers and diblock copolymers comprising:

(a) a biodegradable triblock copolymer present in an amount of 1% to 50% (w/w %) of the total composition having the formula:

$$PLGA_v\text{-}PEG_w\text{-}PLGA_x$$

wherein and v and x are the number of repeat units ranging from 1 to 3,000 and w is the number of repeat units ranging from 3 to 300 and v=x or v≠x;
(b) a biodegradable diblock copolymer present in an amount of 1% to 57% (w/w %) of the total composition having the formula:

$$mPEG_y\text{-}PLGA_z$$

wherein y and z are the number of repeat units with y ranging from 2 to 250 and z ranging from 1 to 3,000, wherein the weight ratio of the sum of the biodegradable triblock copolymer of (a) and the biodegradable diblock copolymer of (b) is 1:19 to 5:1 in said biodegradable drug composition;
(c) at least one additional biodegradable block copolymer; and
(d) at least one pharmaceutically active principle present in an amount of 0.05% to 60% (w/w %) of the total composition wherein the release kinetics of said at least one active principle from said biodegradable drug delivery composition is modulated without affecting physical parameters of said biodegradable drug composition.

Described is a method of modulating the kinetics of release of at least one active principle said method comprising administering a biodegradable drug delivery composition comprising a mixture of at least three triblock copolymers and diblock copolymers comprising:
(a) a biodegradable triblock copolymer having the formula:

$$A_v\text{-}B_w\text{-}A_x$$

wherein A is a polyester and B is polyethylene glycol and v and x are the number of repeat units ranging from 1 to 3,000 and w is the number of repeat units ranging from 3 to 300 and v=x or v≠x;
(b) a biodegradable diblock copolymer having the formula:

$$C_y\text{-}A_z$$

wherein A is a polyester and C is an end-capped polyethylene glycol and y and z are the number of repeat units with y ranging from 2 to 250 and z ranging from 1 to 300 to 250 and z ranging from 1 to 3,000, wherein the weight ratio of the sum of the biodegradable triblock copolymer of (a) and the biodegradable diblock copolymer of (b) is 1:19 to 5:1 in said biodegradable drug composition;
(c) at least one additional biodegradable block copolymer; and
(d) at least one pharmaceutically active principle wherein the release kinetics of said at least one active principle from said biodegradable drug delivery composition is modulated without affecting physical parameters of said biodegradable drug composition.

EXAMPLES

Example 1-Polymer Synthesis

Block copolymers were synthesized according to the method described in U.S. Pat. No. 6,350,812, incorporated herein by reference, with minor modifications. Typically the necessary amount of PEG (in the triblock copolymer) or methoxy-PEG (in the diblock copolymer) was heated at 80° C. and dried under vacuum for 30 minutes in a reactor vessel. DL-lactide (corresponding to the targeted LA/EO molar ratio) and zinc lactate (1/1000 of amount of lactide) were added. The reaction mixture was first dehydrated by two short vacuum/N$_2$ cycles. The reaction was heated at 140° C. under constant nitrogen flow (0.2 bar). After the reaction stopped, the block copolymer was discharged from the vessel and left to stand at room temperature until solidification. The product obtained was characterized by $^1$H NMR for its lactate content. 1H NMR spectroscopy was performed using a Brucker advance 300 MHz spectrometer.

For all 1H NMR spectrograms, MestReNova software was used for the integration of peaks and their analyses. Chemical shifts were referenced to the A=7.26 ppm solvent value for CDCl$_3$.

For the determination of the R ratio, that describes the ratio between lactic acid units over ethylene oxide units (LA/EO), all peaks were separately integrated. The intensity of the signal (integration value) is directly proportional to the number of hydrogens that make the signal. So to determine the R ratio (LA/EO ratio), the integration values need to be homogenous and representative of the same number of protons (e.g. all signal values are determined for 1H). A characteristic peak of PLA and one of PEG are then used to determine the LA/EO ratio. This method is valid for molecular weight of PEGs above 1000 g/mol where the signal obtained for the polymer end-functions can be neglected.

The triblock polymers described herein were labelled PxRy where x represents the molecular weight of the PEG chain in kDa and y is the polyester monomer/ethylene oxide molar ratio, for example the lactic acid/ethylene oxide (LA/EO) molar ratio. The diblock mPEG-PLA polymers described herein where labelled dPxRy where x represents the molecular weight of the PEG chain in kDa and y is the polyester monomer/ethylene oxide molar ratio, for example the lactic acid/ethylene oxide (LA/EO) molar ratio.

Example 2—Preparation of a Specific Formulation for Meloxicam

The formulation F285, described herein, was based on an organic solution of block copolymers containing Meloxicam as API. 1200 milligrams of the block copolymers corresponding to a mix of diblock copolymers and triblock copolymers in defined weight ratio of the sum of triblock to the sum of diblock as indicated in Table 2 were dissolved in 1680 milligrams of DMSO at room temperature over-night and under constant magnetic stirring. The next day 120 milligrams of drug were added to this block copolymer solution and stirred until complete homogenization of the suspension obtained. The formulation was loaded in a syringe before use.

Example 3—Formulation Preparation

Following Examples 1 and 2, the following formulations were prepared as set forth in Tables 1 to 3 below:

All of the compositions in Tables 1 to 3 are completed up to 100% using DMSO as a solvent.

TABLE 1

| N° | TB:DB Weight ratio | Meloxicam % (w/w) | Triblock copolymer 1 PLGA-PEG-PLGA | | mPEG-PLGA Diblock copolymer 1 | | mPEG-PCLA Diblock copolymer 2 | |
|---|---|---|---|---|---|---|---|---|
| | | | % (w/w) | Code | % (w/w) | Code | % (w/w) | Code |
| 295 | 1.00 | 4.00 | 20.00 | (75G)P2R3.5 | 20.00 | (75G)dP0.55R6 | — | — |
| 312 | 1.00 | 4.00 | 20.00 | (75G)P2R3.5 | 10.00 | (75G)dP0.55R6 | 10.00 | (72CL)dP0.35R8.5 |
| 314 | 1.00 | 4.00 | 20.00 | (75G)P2R3.5 | 18.00 | (75G)dP0.55R6 | 2.00 | (72CL)dP0.35R8.5 |

TABLE 2

| N° | TB:DB Weight ratio | Meloxicam % (w/w) | Triblock copolymer 1 PLA-PEG-PLA | | mPEG-PLA Diblock copolymer 1 | | Triblock copolymer 2 PLGA-PEG-PLGA | | mPEG-PLGA Diblock copolymer 2 | |
|---|---|---|---|---|---|---|---|---|---|---|
| | | | % (w/w) | Code | % (w/w) | Code | % (w/w) | Code | % (w/w) | Code |
| 285 | 1.00 | 4.00 | 20.00 | P2R3.5 | 20.00 | dP0.35R8.5 | — | — | — | — |
| 295 | 1.00 | 4.00 | — | — | — | — | 20.00 | (75G)P2R3.5 | 20.00 | (75G)dP0.55R6 |
| 306 | 1.00 | 4.00 | 10.00 | P2R3.5 | 20.00 | dP0.35R8.5 | 10.00 | (75G)P2R3.5 | — | — |
| 307 | 1.00 | 4.00 | 15.00 | P2R3.5 | 20.00 | dP0.35R8.5 | 5.00 | (75G)P2R3.5 | — | — |
| 308 | 1.00 | 4.00 | 18.00 | P2R3.5 | 20.00 | dP0.35R8.5 | 2.00 | (75G)P2R3.5 | — | — |

TABLE 3

| N° | TB:DB Weight ratio | Acetaminophen % (w/w) | Triblock copolymer 1 PLGA-PEG-PLGA | | mPEG-PLGA Diblock copolymer 1 | | mPEG-PCLA Diblock copolymer 2 | |
|---|---|---|---|---|---|---|---|---|
| | | | % (w/w) | Code | % (w/w) | Code | % (w/w) | Code |
| 336 | 1.00 | 4.00 | 20.00 | (75G)P2R3.5 | 20.00 | (75G)dP0.55R6 | — | — |
| 337 | 1.00 | 4.00 | 20.00 | (75G)P2R3.5 | 10.00 | (75G)dP0.55R6 | 10.00 | (72CL)dP0.35R8.5 |
| 338 | 1.00 | 4.00 | 20.00 | (75G)P2R3.5 | 15.00 | (75G)dP0.55R6 | 5.00 | (72CL)dP0.35R8.5 |
| 339 | 1.00 | 4.00 | 20.00 | (75G)P2R3.5 | 18.00 | (75G)dP0.55R6 | 2.00 | (72CL)dP0.35R8.5 |

Example 4-Injectability of Differing Compositions

Injectability measurements are performed using the Lloyd Instruments FT plus texturometer, using the following analytical conditions: 500 µL of studied formulation are injected through a 1 mL Codan syringe, a 23G 1" Terumo needle with a 1 mL/min flow rate. Samples are analyzed in six replicates.

The obtained value in N (Newtons) is correlated with the needed force to inject the formulation with the described conditions.

Figure 1:
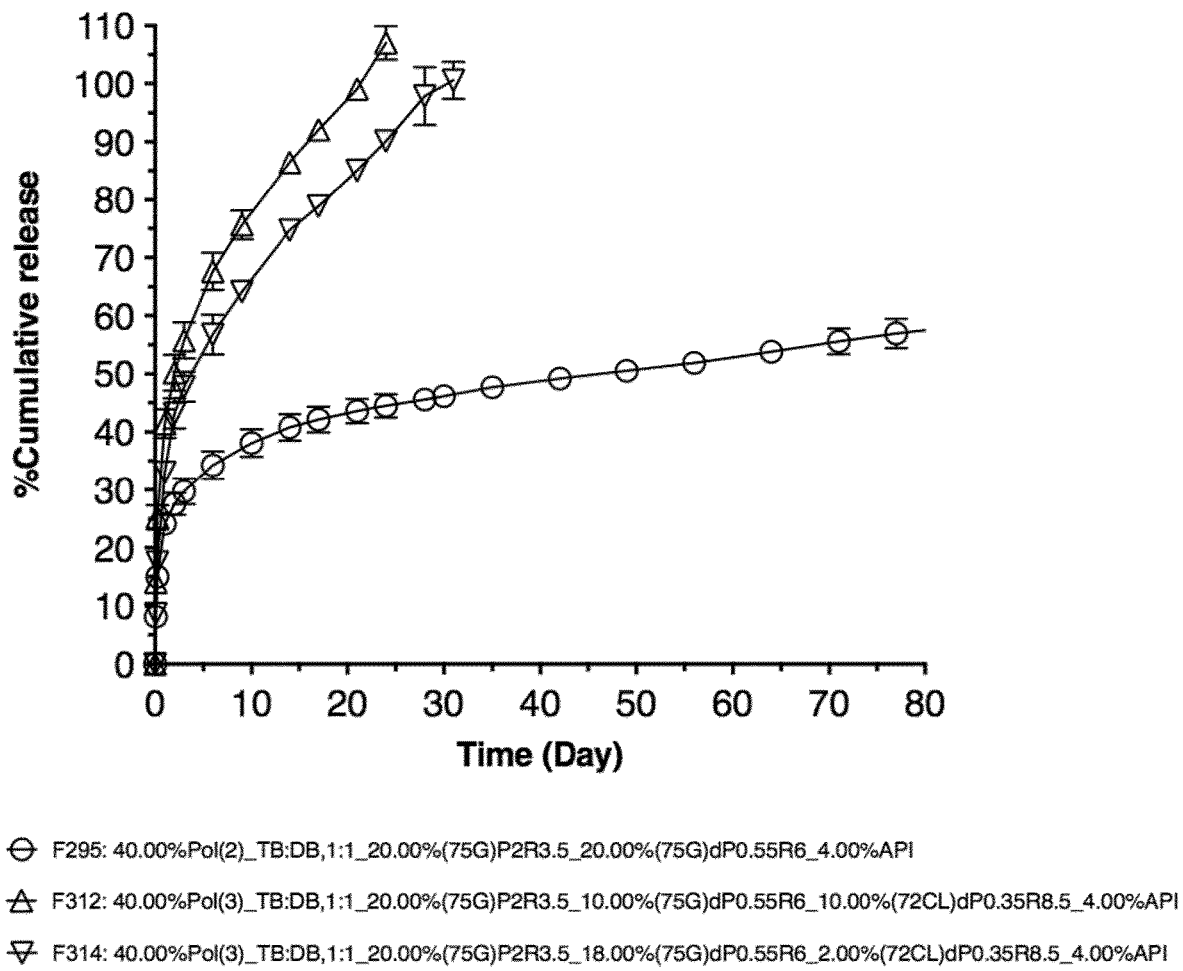
FIG. 1 displays the in vitro cumulative release of meloxicam over time from three different formulations. Formulation F295 (○) has a weight ratio of the sum of triblock to diblock of 1 containing 20.00% of (75G)P2R3.5 triblock copolymer and 20.00% of (75G)dP0.55R6 diblock copolymer with 4.00% active principle (API) and 56.00% of DMSO. Formulation F312 (Δ) has a weight ratio of the sum of triblock to diblock of 1 containing 20.00% of (75G) P2R3.5 triblock copolymer, 10.00% of (75G)dP0.55R6 and 10.00% (72CL)dP0.35R8.5 diblock copolymer with 4.00% active principle (API) and 56.00% of DMSO. Formulation F314 (∇) has a weight ratio of the sum of triblock to diblock of 1 containing 20.00% of (75G)P2R3.5 triblock copolymer, 18.00% (75G)dP0.55R6 and 2.00% (72CL)dP0.35R8.5 diblock copolymer with 4.00% active principle (API) and 56.00% of DMSO. The specific block copolymer formulations are set forth in Table 1 below.

Example from FIG. 1:

F295, F312 and F314 are mixtures of triblock (TB) (75G)P2R3.5 and diblock (DB) (75G)dP0.55R6 or mixtures of triblock (TB) (75G)P2R3.5, diblock (DB) (75G) dP0.55R6 and (72CL)dP0.35R8.5 respectively for a total polymer content of 40% as indicated in Table 1. Injectability average values for F295, F312 and F314 are 11.9N and 11.4N and 12.1N respectively as indicated in Table 4.

Data show that the addition of an additional biodegradable block copolymer induces a release modulation, as shown in FIG. 1, without having an impact on injectability.

TABLE 4

| N° | Meloxicam % (w/w) | Total copolymer content (%) | Number of copolymers | Number of replicates | Injectability (N) | Standard deviation |
|---|---|---|---|---|---|---|
| 295 | 4.00 | 40.00 | 2 | 6 | 11.9 | 0.7 |
| 312 | 4.00 | 40.00 | 3 | 6 | 11.6 | 1.1 |
| 314 | 4.00 | 40.00 | 3 | 6 | 12.1 | 0.7 |

Example from FIG. 3:

F285, F295, F306, F307 and F308 are mixtures of triblock (TB) P2R3.5 and diblock (DB) dP0.35R8.5 or mixtures of triblock (TB) (75G)P2R3.5 and diblock (DB) dP0.35R8.5 or mixtures of triblock (TB) P2R3.5 and (75G) P2R3.5 and diblock (DB) dP0.35R8.5 respectively for a total polymer content of 40% as indicated in Table 2. Injectability average values for F285, F295, F306, F307 and F308 are 8.7N, 11.8N, 8.9N, 8.3N and 9.4N respectively as indicated in Table 5.

Data show that the addition of an additional biodegradable block copolymer induces a release modulation, as shown in FIG. 3, without having an impact on injectability.

TABLE 5

| N° | Meloxicam % (w/w) | Total copolymer content (%) | Number of copolymers | Number of replicates | Injectability (N) | Standard deviation |
|---|---|---|---|---|---|---|
| 285 | 4.00 | 40.00 | 2 | 6 | 8.7 | 0.3 |
| 295 | 4.00 | 40.00 | 2 | 6 | 11.8 | 0.7 |
| 306 | 4.00 | 40.00 | 3 | 6 | 8.9 | 0.4 |
| 307 | 4.00 | 40.00 | 3 | 6 | 8.3 | 0.6 |
| 308 | 4.00 | 40.00 | 3 | 6 | 9.4 | 0.4 |

Example from FIG. 5:

F336, F337, F338 and F339 are mixtures of triblock (TB) (75G)P2R3.5 and diblock (DB) (75G)dP0.55R6 or mixtures of triblock (TB) (75G)P2R3.5 and diblock (DB) (75G) dP0.55R6 and (72CL)dP0.35R8.5 respectively for a total polymer content of 40% as indicated in Table 3. Injectability average values for F336, F337, F338 and F339 are 12.6N, 11.1N, 10.7N and 11.6N respectively as indicated in Table 6.

Data show that the addition of an additional biodegradable block copolymer induces a release modulation, as shown in FIG. 5, without having an impact on injectability.

TABLE 6

| N° | Acetaminophen % (w/w) | Total copolymer content (%) | Number of copolymers | Number of replicates | Injectability (N) | Standard deviation |
|---|---|---|---|---|---|---|
| 336 | 4.00 | 40.00 | 2 | 6 | 12.6 | 1.0 |
| 337 | 4.00 | 40.00 | 3 | 6 | 11.1 | 0.5 |
| 338 | 4.00 | 40.00 | 3 | 6 | 10.7 | 0.6 |
| 339 | 4.00 | 40.00 | 3 | 6 | 11.6 | 0.5 |

Example 5—Viscosity Measurements

Dynamic viscosity is determined using an Anton Paar Rheometer equipped with cone plate measuring system. The following set-up is typically used to measure viscosity:

600 µL of studied formulation are placed on the measuring plate. The temperature is controlled at +35° C. The measuring system used is a cone plate with a diameter of 50 mm and a cone angle of 1 degree (CP50-1).

The working range is from 1000 to 10 Hz.

After being vortexed for 30 sec, formulations are placed at the center of the thermo-regulated measuring plate using a spatula. The measuring system is lowered down and a 0.104 mm gap is left between the measuring system and the measuring plate.

Eleven viscosity measurement points are determined across the 1000 to 10 Hz shear rate range. Given values are the one obtained at 100 Hz.

Example from FIG. 5:

F336, F337, F338 and F339 are mixtures of triblock (TB) (75G)P2R3.5 and diblock (DB) (75G)dP0.55R6 or mixtures of triblock (TB) (75G)P2R3.5 and diblock (DB) (75G) dP0.55R6 and (72CL)dP0.35R8.5 respectively for a total polymer content of 40% as indicated in Table 3. Viscosity average values for F336, F337, F338 and F339 are 465 mPa·s, 454 mPa·s, 446 mPa·s and 438 mPa·s respectively as indicated in Table 7.

Data show that the addition of an additional biodegradable block copolymer induces a release modulation, as shown in FIG. 5, without having an impact on dynamic viscosity.

TABLE 7

| N° | Acetaminophen % (w/w) | Total copolymer content (%) | Number of copolymers | Number of replicates | Viscosity at 100s-1 35° C. (mPa.s) | Standard deviation |
|---|---|---|---|---|---|---|
| 336 | 4.00 | 40.00 | 2 | 6 | 465 | 3 |
| 337 | 4.00 | 40.00 | 3 | 6 | 454 | 12 |
| 338 | 4.00 | 40.00 | 3 | 6 | 446 | 2 |
| 339 | 4.00 | 40.00 | 3 | 6 | 438 | 1 |

Example 6—In Vitro Release Assay 50 mg of meloxicam formulation is added to 50 ml of physiological buffer. The physiological buffer that is used is phosphate-buffered saline (PBS) pH 7.4, which is 137 mM Sodium Chloride, 2.7 mM Potassium Chloride, 10 mM Disodium Phosphate, 1.8 mM Monopotassium Phosphate and 0.1% sodium azide. Upon injection, the solvent diffuses away from the formulation and the remaining polymer forms an in situ depot within the aqueous environment.

In order to maintain sink conditions, for drug release, the release medium is maintained under constant shaking at 180 rpm (Unimax 1010 apparatus, Heidolph) at 37° C. At pre-determined time intervals, media are collected and analyzed by UPLC. The amount of meloxicam released from the formulation is calculated from a calibration curve. The concentration of meloxicam ranges between 0 and 160 µg/ml.

The meloxicam incorporated into the polymer solution is encapsulated within the polymer matrix as it solidifies.

Example 7—In Vivo Testing

The compositions according to the invention may be tested in a pharmacokinetic study in a relevant animal species (rat, dog, minipig). Compositions containing x mg of drug per animal of the formulations herein may be subcutaneously administered to animals. Blood samples are collected into tubes (with or without anticoagulant) at different time points, optionally centrifuged and the matrix (plasma, serum, whole blood) from each time point retained. The samples are analyzed by LC/MS/MS and quantified for drug content. Results are presented as ng/ml or pg/mL of matrix measured over time. A result with a sustained matrix level of a drug within its therapeutic window means that the compositions according to the invention are effective in sustaining a slow release over a time up to X months.

While the invention has been described in terms of various preferred embodiments, the skilled artisan will appreciate that various modifications, substitutions, omissions and changes may be made without departing from the scope thereof. Accordingly, it is intended that the scope of the present invention be limited by the scope of the claims, including equivalents thereof.

The invention claimed is:

1. An injectable biodegradable drug delivery composition comprising:
   (i) a mixture of at least three different block copolymers, wherein each block copolymer is:
   (a) a biodegradable triblock copolymer having the formula:

$A_v\text{-}B_w\text{-}A_x$ wherein A is a polyester and B is polyethylene glycol and v and x are the number of repeat units ranging from 1 to 3,000 and w is the number of repeat units ranging from 3 to 300 and v=x or v≠x; or
   (b) a biodegradable diblock copolymer having the formula:

$C_y\text{-}A_z$ wherein A is a polyester and C is an end-capped polyethylene glycol and y and z are the number of repeat units with y ranging from 2 to 250 and z ranging from 1 to 3,000; and
   wherein the mixture comprises at least one (a) and at least one (b); and the weight ratio of the sum of the biodegradable triblock copolymers of (a) and the sum of the biodegradable diblock copolymers of (b) is 1:19 to 5:1; and wherein for at least one of the copolymers according to (a) or (b) A is poly(lactic-co-glycolic acid) (PLGA); and
   (ii) at least one pharmaceutically active ingredient;
   wherein the release kinetics of said at least one active ingredient from said biodegradable drug delivery composition can be modulated without adversely affecting injectability and/or viscosity before injection of the injectable biodegradable drug delivery composition and/or depot robustness after injection of the biodegradable drug delivery composition, compared to a composition having a single biodegradable triblock of the copolymer of (a) and a single biodegradable diblock of the copolymer of (b).

2. The injectable biodegradable drug delivery composition according to claim 1, wherein for at least one biodegradable triblock copolymer (a) A is PLGA.

3. The injectable biodegradable drug delivery composition according to claim 1, wherein for at least one biodegradable diblock copolymer (b) A is PLGA.

4. The injectable biodegradable drug delivery composition according to claim 1, comprising a copolymer as defined in (a) or (b) wherein when said polyester A is not PLGA, A is selected from the group of a polylactic acid (PLA), polyglycolic acid, polycaprolactone, poly(ε-caprolactone-co-lactide) (PCLA), polyethylene adipate, polyhydroxyalkanoate and mixtures thereof and optionally wherein the end-capped polyethylene glycol is methoxy polyethylene glycol.

5. The injectable biodegradable drug delivery composition according to claim 4, wherein when said polyester A is not PLGA, A is PLA.

6. The injectable biodegradable drug delivery composition according to claim 4, wherein when said polyester A is not PLGA, A is PCLA.

7. The injectable biodegradable drug delivery composition according to claim 1 which further comprises at least one organic solvent.

8. The injectable biodegradable drug delivery composition according to claim 1, which composition further comprises:
   (a) a biodegradable triblock copolymer having the formula:

$PLGA_v\text{-}PEG_w\text{-}PLGA_x$ wherein v and x are the number of repeat units ranging from 1 to 3,000 and w is the number of repeat units ranging from 3 to 300 and v=x or v≠x; and/or
   (b) a biodegradable diblock copolymer having the formula:

$mPEG_y\text{-}PLGA_z$ wherein y and z are the number of repeat units with y ranging from 2 to 250 and z ranging from 1 to 3,000.

9. The injectable biodegradable drug delivery composition according to claim 1, which composition further comprises:
   (a) a biodegradable triblock copolymer having the formula:

$PCLA_v\text{-}PEG_w\text{-}PCLA_x$ wherein v and x are the number of repeat units ranging from 1 to 3,000 and w is the number of repeat units ranging from 3 to 300 and v=x or v≠x; and/or (b) a biodegradable diblock copolymer having the formula:

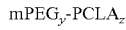
mPEG$_y$-PCLA$_z$ wherein y and z are the number of repeat units with y ranging from 2 to 250 and z ranging from 1 to 3,000.

10. The injectable biodegradable drug delivery composition according to claim 1, which composition further comprises:
(a) a biodegradable triblock copolymer having the formula:

PLA$_v$-PEG$_w$-PLA$_x$ wherein v and x are the number of repeat units ranging from 1 to 3,000 and w is the number of repeat units ranging from 3 to 300 and v=x or v≠x; and/or
(b) a biodegradable diblock copolymer having the formula:

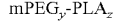
mPEG$_y$-PLA$_z$ wherein y and z are the number of repeat units with y ranging from 2 to 250 and z ranging from 1 to 3,000.

11. The injectable biodegradable drug delivery composition according to claim 1, wherein the mass of the polyethylene glycol chain ranges from 180 g/mol to 12 kg/mol or 194 g/mol to 12 kg/mol or 200 g/mol to 12 kg/mol or from 100 g/mol to 4 kg/mol and the molecular weight of the end-capped polyethylene glycol chain ranges from 100 g/mol to 2 kg/mol or 164 g/mol to 10 kg/mol.

12. The injectable biodegradable drug delivery composition according to claim 1, further comprising a pharmaceutically acceptable vehicle.

13. The injectable biodegradable drug delivery composition according to claim 1 wherein the at least one pharmaceutically active ingredient is hydrophobic.

14. The injectable biodegradable drug delivery composition according to claim 1 wherein the at least one pharmaceutically active ingredient is meloxicam, acetaminophen or combinations thereof.

15. The injectable biodegradable drug delivery composition according to claim 1, wherein the at least one pharmaceutically active ingredient is present in an amount of from 0.05% to 60% (w/w %) of the total composition.

16. The injectable biodegradable drug delivery composition according to claim 15 which is an injectable liquid and wherein the at least one pharmaceutically active ingredient is present in an amount of 0.05% to 60% (w/w %).

17. The injectable biodegradable drug delivery composition according to claim 1, wherein the mixture of at least three different block copolymers is present in an amount of 2% to 60% (w/w %) of the total composition.

18. The injectable biodegradable drug delivery composition according to claim 1, wherein the one or more triblock copolymers are present in an amount of 1% to 50% (w/w %) of the total composition.

19. The injectable biodegradable drug delivery composition according to claim 1, wherein the one or more diblock copolymers are present in an amount of 1% to 57% (w/w %) of the total composition.

20. The injectable biodegradable drug delivery composition according to claim 1 wherein the weight ratio of the sum of the biodegradable triblock copolymers of (a) over the sum of the biodegradable diblock copolymers of (b) in said biodegradable drug delivery composition is 1:5 to 3:1.

21. The injectable biodegradable drug delivery composition according to claim 1, wherein for each of the block copolymers in the composition, the polyester repeat unit to ethylene oxide molar ratio in the composition is between 0.5 to 22.3 in the triblock(s) and 0.8 to 15 in the diblock(s).

22. The injectable biodegradable drug delivery composition according to claim 1, which composition comprises three different block copolymers or four different block copolymers or five different block copolymers or six different block copolymers.

23. The injectable biodegradable drug delivery composition according to claim 1 which comprises one biodegradable triblock copolymer, or two different biodegradable triblock copolymers, or three different biodegradable triblock copolymers, or four different biodegradable triblock copolymers.

24. The injectable biodegradable drug delivery composition according to claim 1 which comprises one biodegradable diblock copolymer, or two different biodegradable diblock copolymers, or three different biodegradable diblock copolymers, or four different biodegradable diblock copolymers.

25. The injectable biodegradable drug delivery composition according to claim 1 comprising a triblock copolymer present in an amount of 1% to 50% (w/w %) of the total composition, a diblock copolymer present in an amount of 1% to 57% (w/w %) of the total composition, and one or more further diblock or triblock copolymers each present in an amount of 0.5% to 20% (w/w %) of the total composition.

26. The injectable biodegradable drug delivery composition according to claim 1 which is a composition according to composition No. 312, 314, 306, 307, 308, 337, 338, or 339 as defined below:
composition 312: meloxicam in an amount of 4.00 (w/w %), (75G)P2R3.5 in an amount of 20.00 (w/w %), (75G)dP0.55R6 in an amount of 10.00 (w/w %), and (72CL)dP0.35R8.5 in an amount of 10.00 (w/w %);
composition 314: meloxicam in an amount of 4.00 (w/w %), (75G)P2R3.5 in an amount of 20.00 (w/w %), (75G)dP0.55R6 in an amount of 18.00 (w/w %), and (72CL)dP0.35R8.5 in an amount of 2.00 (w/w %);
composition 306: meloxicam in an amount of 4.00 (w/w %), P2R3.5 in an amount of 10.00 (w/w %), dP0.35R8.5 in an amount of 20.00 (w/w %), and (75G)P2R3.5 in an amount of 10.00 (w/w %);
composition 307: meloxicam in an amount of 4.00 (w/w %), P2R3.5 in an amount of 15.00 (w/w %), dP0.35R8.5 in an amount of 20.00 (w/w %), and (75G)P2R3.5 in an amount of 5.00 (w/w %);
composition 308: meloxicam in an amount of 4.00 (w/w %), P2R3.5 in an amount of 18.00 (w/w %), dP0.35R8.5 in an amount of 20.00 (w/w %), and (75G)P2R3.5 in an amount of 2.00 (w/w %);
composition 337: acetaminophen in an amount of 4.00 (w/w %), (75G)P2R3.5 in an amount of 20.00 (w/w %), (75G)dP0.55R6 in an amount of 10.00 (w/w %), and (72CL)dP0.35R8.5 in an amount of 10.00 (w/w %);
composition 338: acetaminophen in an amount of 4.00 (w/w %), (75G)P2R3.5 in an amount of 20.00 (w/w %), (75G)dP0.55R6 in an amount of 15.00 (w/w %), and (72CL)dP0.35R8.5 in an amount of 5.00 (w/w %);
composition 339: acetaminophen in an amount of 4.00 (w/w %), (75G)P2R3.5 in an amount of 20.00 (w/w %), (75G)dP0.55R6 in an amount of 18.00 (w/w %), and (72CL)dP0.35R8.5 in an amount of 2.00 (w/w %);
wherein each triblock copolymer is labelled PxRy where x represents the molecular weight of the PEG chain in kDa and y is the polyester monomer/ethylene oxide molar ratio; each diblock copolymer is labelled dPxRy where x represents the molecular weight of the PEG chain in kDa and y is the polyester monomer/ethylene oxide molar ratio; the term 75G specifies that the polyester is PLGA wherein the LA/GA molar ratio is 75; and the term 72CL specifies that the polyester is PCLA wherein the LA/CL molar ratio is 72, and for all other polymers the polyester is PLA.

27. The injectable biodegradable drug delivery composition according to claim 1, wherein the release of at least one active ingredient can be modulated.

28. The injectable biodegradable drug delivery composition according to claim 1, which is suitable to deliver the active ingredient to a subject for at least 1 day.

29. The injectable biodegradable drug delivery composition according to claim 1 which is suitable for parenteral administration.

30. The injectable biodegradable drug delivery composition according to claim 1 wherein the block copolymers have less than 5% (w/w) solubility in an aqueous solution.

31. A method of modulating the kinetics of release of at least one active ingredient, said method comprising administering the injectable biodegradable drug delivery composition as defined in claim 1 to a subject, wherein the release kinetics of said at least one active ingredient from said biodegradable drug delivery composition are modulated without adversely affecting injectability and/or viscosity before injection of the injectable biodegradable drug delivery composition and/or depot robustness after injection of said biodegradable drug delivery composition.

* * * * *